US011776693B2

(12) United States Patent
Zira et al.

(10) Patent No.: US 11,776,693 B2
(45) Date of Patent: Oct. 3, 2023

(54) CONVERSATIONAL SERVICES FOR ARTIFICIAL INTELLIGENCE HEALTH SUPPORT

(71) Applicant: Lark Technologies, Inc., Mountain View, CA (US)

(72) Inventors: Jeff Zira, Mountain View, CA (US); Jared Cordova, Sunnyvale, CA (US); Stephanie Hilliard, Portland, OR (US)

(73) Assignee: Lark Technologies, Inc., Mountain View, CA (US)

( * ) Notice: Subject to any disclaimer, the term of this patent is extended or adjusted under 35 U.S.C. 154(b) by 42 days.

(21) Appl. No.: 17/514,394

(22) Filed: Oct. 29, 2021

(65) Prior Publication Data
US 2022/0319702 A1    Oct. 6, 2022

Related U.S. Application Data

(63) Continuation of application No. 17/222,732, filed on Apr. 5, 2021, now Pat. No. 11,417,428.

(51) Int. Cl.
*G16H 20/60* (2018.01)
*G16H 50/20* (2018.01)

(52) U.S. Cl.
CPC ............. *G16H 50/20* (2018.01); *G16H 20/60* (2018.01)

(58) Field of Classification Search
CPC ... G06Q 50/22–24; G16H 50/20; G16H 20/60
See application file for complete search history.

(56) References Cited

U.S. PATENT DOCUMENTS

| 11,056,223 B1* | 7/2021 | Ahmad ................. G16H 10/20 |
| 2009/0177495 A1 | 7/2009 | Abousy |
| 2014/0058724 A1 | 2/2014 | Barve |

(Continued)

FOREIGN PATENT DOCUMENTS

WO    WO 13/033655    3/2013

OTHER PUBLICATIONS

"Lark and Omron use AI to reduce blood pressure"; Steve Rogerson; IoT M2M Council; Oct. 1, 2019; (Year: 2019).*

(Continued)

*Primary Examiner* — John A Pauls
(74) *Attorney, Agent, or Firm* — Brownstein Hyatt Farber Schreck, LLP

(57) ABSTRACT

A system provides artificial intelligence health support for people. The system renders specific, targeted treatments for people by using a flow engine and a conversational service to call one or more conversational modules. The treatments for the people may be tracked. The flow engine and/or one or more of the modules may include different instructions to perform for different programs and/or goals that have been configured. The flow engine and/or one or more of the conversational modules may also include instructions to perform when certain features are active (which may be activated when certain programs and/or goals are configured), when data regarding activity for people are received, and so on. Other modules may be dedicated to particular programs and/or goals. Some modules may determine whether or not to perform various instructions repetitiously, and/or may determine to do so when a priority of a previous instruction is below a threshold.

20 Claims, 14 Drawing Sheets

(56) References Cited

U.S. PATENT DOCUMENTS

| | | | | |
|---|---|---|---|---|
| 2014/0089836 | A1* | 3/2014 | Damani | G16H 20/10 715/771 |
| 2015/0294595 | A1 | 10/2015 | Hu et al. | |
| 2016/0063204 | A1 | 3/2016 | Srinivasan | |
| 2019/0297033 | A1 | 9/2019 | Harma et al. | |
| 2021/0098105 | A1 | 4/2021 | Lee | |
| 2022/0351861 | A1 | 11/2022 | Zira et al. | |

OTHER PUBLICATIONS

"Study Shows Lark Leads to Blood Pressure Reduction of 8.4/6.4 mm Hg"; lark.com/press-articles/; Sep. 17, 2019; (Year: 2019).*

Imran et al., "Comprehensive Survey of IoT, Machine Learning, and Blockchain for Health Care Applications: A Topical Assessment for Pandemic Preparedness, Challenges, and Solutions" 2021 Electronics 10:2051 (37 pages).

Lark's Hypertension Management Program, Study Shows Lark Leads to Blood Pressure Reduction of 8.4/6.4 mm Hg, Sep. 17, 2019, https://www.lark.com/press-articles/study-shows-lark-leads-to-blood-pressure- reduction-of-8-4-6-4-mm-hg, 5 pages.

Rogerson, "Lark and Omron use AI to reduce blood pressure," IoT M2M Council, Oct. 1, 2019, https://naylor.iotm2mcouncil.org/omrolark, 4 pages.

U.S. Appl. No. 17/222,706, filed Apr. 5, 2021, Zira et al.

U.S. Appl. No. 17/222,732, filed Apr. 5, 2021, Zira et al.

Dang, "Software Engineering: Bes Practices for Reusing in Software Development," Mar. 17, 2021, gitconnected.com (Year: 2021), 10 pages.

Lark Website, "Lark for Hypertension is Proven," www.lark.com/hypertension; captured from the internet archive Nov. 16, 2019; https://web.archive.org/web/20191116220024/www.lark.com/hypertension, 9 pages.

Lark, "10 areas in which AI will transform primary care," featuring Lark Health for "digital Health coaching tools for diabetes, hypertension, and obesity," Sep. 6, 2019, 1 page.

Lark, Diabetes A1c Improvement, known at least as early as Apr. 5, 2021, 2 pages.

Lark, The Chronic Disease Problem, Future of Health Presentation, known at least as early as Apr. 5, 2021, 14 pages.

Lark, The Diabetes Problem, Summit Slides, known at least as early as Apr. 5, 2021, 14 pages.

Lark, Well360: Strategic Partnership with Lark, known at least as early as Apr. 5, 2021, 20 pages.

Lark, Chronic Disease Prevention and Management, known at least as early as Apr. 5, 2021, 8 pages.

Lark, Chronic Disease Prevention and Management, known at least as early as Apr. 5, 2021, 13 pages.

Lark, Diabetes Prevention Program One Page Flyer, known at least as early as Apr. 5, 2021, 1 page.

Lark, Food Feature Enhancements, known at least as early as Apr. 5, 2021, 6 pages.

Lark for Hypertension is Proven, known at least as early as Apr. 5, 2021, 9 pages.

Lark HYT Webinar, Oct. 2019, 30 pages.

Lark is an Integrated Solution, known at least as early as Apr. 5, 2021, 6 pages.

Lark Product Training All Programs Generic, known at least as early as Apr. 5, 2021, 43 pages.

Lark, Virtual Coaching Platform, known at least as early as Apr. 5, 2021, 2 pages.

Lark, Virtual Coaching Platform, known at least as early as Apr. 5, 2021, 11 pages.

Lark, Virtual Coaching Platform, known at least as early as Apr. 5, 2021, 1 page.

Lark, Well360: Strategic Partnership CAB, known at least as early as Apr. 5, 2021, 20 pages.

Lark Hypertension Care Program, Oct. 1, 2019, 20 pages.

Lark Wellness Program, Jul. 2019, 15 pages.

Stein et al., Lark's A.I for Diabetes Study Shows that Patients Significantly Reduce A1c, known at least as early as Apr. 5, 2021, 8 pages.

Lark, The Future of Disease Prevention and Management, known at least as early as Apr. 5, 2021, 2 pages.

Trigger Graphic, known at least as early as Apr. 5, 2021, 1 page.

Lark, Well360: Strategic Partnership with Lark, known at least as early as Apr. 5, 2021, 2 pages.

Upadhyay, "What is a Modular Design? Everything You Want to Know in 8 Easy Answers!," Nov. 9, 2020, jigsawacademy.com, 8 pages.

* cited by examiner

CONVERSATIONAL SERVICES FOR ARTIFICIAL INTELLIGENCE HEALTH SUPPORT

CROSS-REFERENCE TO RELATED APPLICATION

This application is a continuation of U.S. patent application Ser. No. 17/222,732, filed Apr. 5, 2021, the contents of which are incorporated herein by reference as if fully disclosed herein.

FIELD

The described embodiments relate generally to artificial intelligence. More particularly, the present embodiments relate to conversational services for artificial intelligence health support for users that renders specific, targeted treatment for the users and tracks those treatments.

BACKGROUND

Medical costs continue to rise. The advantages of regular medical care are not disputed. The relationship between how invested people are in their care and the quality of medical attention is also not disputed. However, it is simply not always medically feasible to have an entire staff of doctors and other medical professionals work with every patient at every step of the way.

As time goes on, the medical field finds more and more ways to shift more of medical care to lower cost options without sacrificing care. Urgent care centers are used for visits that are not serious enough to justify a trip to the hospital. Nurse practitioners provide care that is not serious enough to require a full doctor. Coaches of various types can even aid people in dealing with the day-to-day addressing of various conditions that simply cannot be practically or economically dealt with through more expensive and/or advanced medical professionals.

SUMMARY

The present disclosure relates to systems, methods, apparatuses, and computer program products for providing artificial intelligence health support for people. Specific, targeted treatments for people may be rendered by using a flow engine to call one or more conversational services. The specific, targeted treatments for the people may be tracked. The flow engine and/or one or more of the conversational services may include different instructions to perform for different programs and/or goals that have been configured for people. The flow engine and/or one or more of the conversational services may also include instructions to perform when certain features are active (which may be activated when certain programs and/or goals are configured for people), when data regarding activity for people are received, and so on. Other conversational services may be dedicated to particular programs and/or goals. Some conversational services may determine whether or not to perform various instructions repetitiously, such as determining not to perform such instructions repetitiously when a priority of a previous instruction is below a threshold.

In various embodiments, a system for interacting with a database to provide artificial intelligence health support for people includes a memory allocation configured to store at least one executable asset and a processor allocation configured to access the memory allocation and execute the at least one executable asset to instantiate a conversational service and an artificial intelligence health support service. The conversational service renders a first specific, targeted treatment for a first person in association with a first program that is configured for the first person using a conversational module of conversational modules and first user information retrieved from the database and renders a second specific, targeted treatment for a second person in association with a second program that is configured for the second person using the conversational module of the conversational modules includes first instructions to perform for the first program and second instructions to perform for the second program. The artificial intelligence health support service tracks the first specific, targeted treatment in first user progress stored in the database and tracks the first specific, targeted treatment in second user progress stored in the database.

In some examples, the conversational module is a first conversational module and the conversational service further renders the first specific, targeted treatment for the first person using a second conversational module that is dedicated to the first program. In various implementations of such examples, the conversational service further renders the second specific, targeted treatment for the second person using a third conversational module that is dedicated to the second program.

In a number of examples, the conversational module is a first conversational module and the conversational service further renders the first specific, targeted treatment for the first person using a second conversational module when a feature is active. In various examples, at least one of the conversational modules performs a set of instructions repetitiously. In some examples the conversational module is a first conversational module and the conversational service further renders the first specific, targeted treatment for the first person using a second conversational module upon receiving data regarding activity for the first person. In a number of examples, at least one of the conversational modules is operable to change the first program for the first person.

In some embodiments, a system for interacting with a database to provide artificial intelligence health support for people includes a memory allocation configured to store at least one executable asset and a processor allocation configured to access the memory allocation and execute the at least one executable asset to instantiate a conversational service and an artificial intelligence health support service. The conversational service renders a specific, targeted treatment for a first person and a second person using a conversational module of conversational modules and first user information for the first person and second user information for the second person retrieved from the database. The conversational module includes first instructions to perform for a first goal configured for the first person and second instructions to perform for a second goal configured for the second person. The artificial intelligence health support service tracks the specific, targeted treatment in first user progress and second user progress stored in the database.

In various examples, at least one of the conversational modules is operable to change the first goal for the first person. In some examples, the conversational module is a first conversational module and the conversational service further renders the specific, targeted treatment for the first person or the second person using a second conversational module upon receiving data regarding activity for the first person or the second person. In a number of examples, at least one of the conversational modules performs a set of instructions repetitiously when a priority of a previous action is below a threshold.

In some examples, the conversational module is a first conversational module and the conversational service further renders the specific, targeted treatment for the first person or the second person using a second conversational module when a feature is active. In a number of examples, the conversational module is a first conversational module and the conversational service further renders the specific, targeted treatment for the first person using a second conversational module that is dedicated to the first goal. In various implementations of such examples, the conversational service further renders the specific, targeted treatment for the second person using a third conversational module that is dedicated to the second goal.

In a number of embodiments, a system for interacting with a database to provide artificial intelligence health support for people includes a memory allocation configured to store at least one executable asset and a processor allocation configured to access the memory allocation and execute the at least one executable asset to instantiate a conversational service and an artificial intelligence health support service. The conversational service renders a specific, targeted treatment for a first person and a second person using first user information for the first person and second user information for the second person retrieved from the database by using a flow engine and at least one of the conversational modules. The flow engine includes first instructions to perform for a first program or a first goal configured for the first person and second instructions to perform for a second program or a second goal configured for the second person. The artificial intelligence health support service tracks the specific, targeted treatment in first user progress and second user progress stored in the database.

In various examples, the first program or the first goal configured for the first person may be the first program, the second program of the second goal configured for the second person may be the second program, the flow engine further includes third instructions to perform for the first goal configured for the first person, and the flow engine further includes fourth instructions to perform for the second goal configured for the second person. In some examples, the flow engine includes a third set of instructions to perform for the first person and the second person regardless of any program or goal configured for the first person or the second person.

In a number of examples, the flow engine includes third instructions to perform when a feature is active. In various implementations of such examples, the feature is activated upon configuration of the first goal or the first program for the first person. In some examples, the flow engine includes third instructions to perform upon receiving data regarding activity for the first person or the second person.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1:
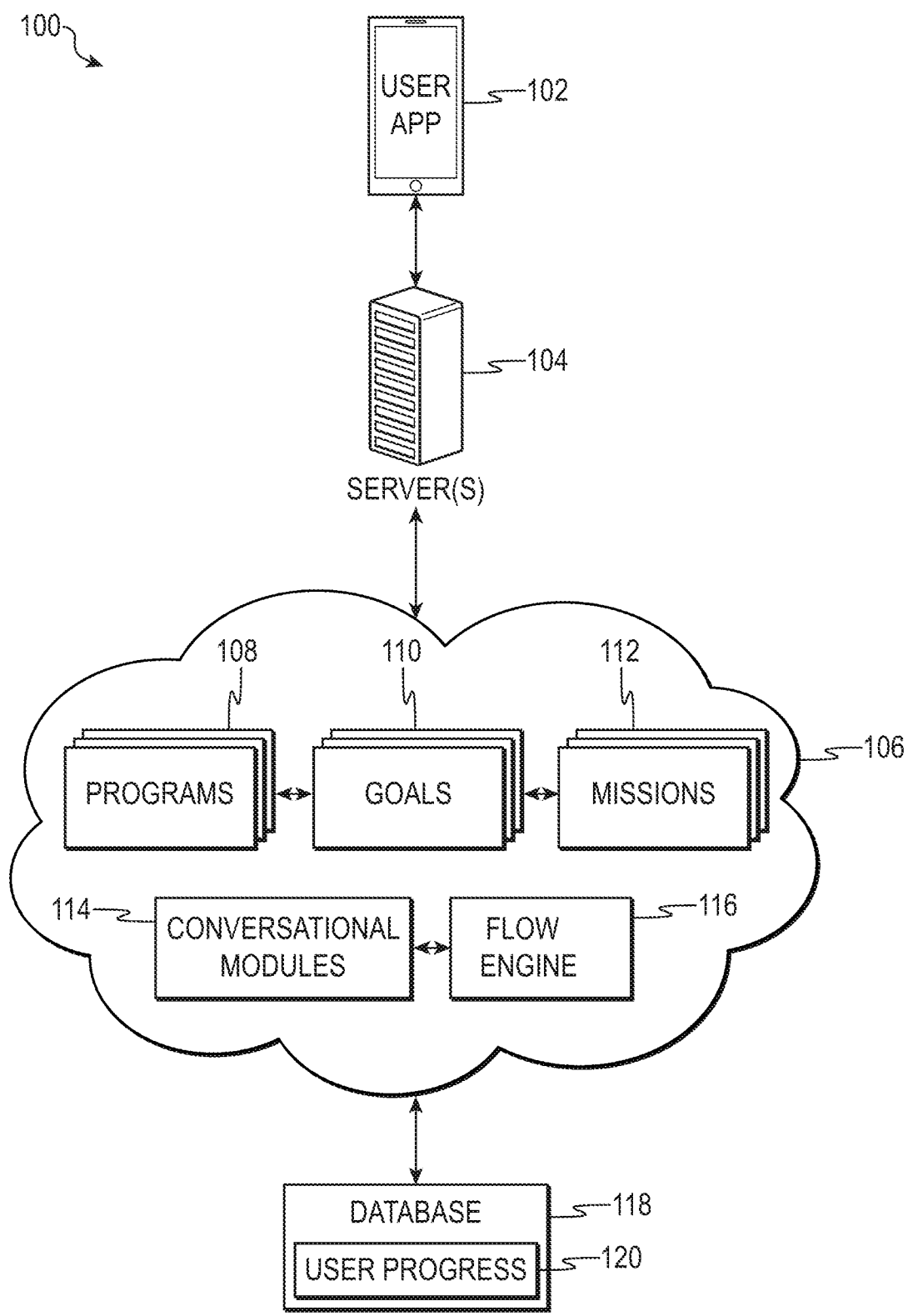
FIG. 1 depicts an example system for providing artificial intelligence health support for people that renders specific, targeted treatment for the people and tracks those treatments.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, apparatuses, methods, and computer program products that embody various elements of the present disclosure. However, it should be understood that the described disclosure may be practiced in a variety of forms in addition to those described herein.

Even coaches may not have the available time to help all people address all conditions. Even if they did, not everyone can afford to have human coaches aid them with all of the conditions they may need to address. Artificial intelligence health support may step in where human coaches fall down, but such artificial intelligence health support may be most valuable when it can handle as many functions with as much responsiveness as human coaches. If the artificial intelligence health support does not seem human enough or competent enough, people may not use them.

Further, artificial intelligence health support may require a great deal of effort to configure and may not enable a great deal of flexibility. Different people may have a great deal of different needs from artificial intelligence health support and a great deal of effort may go into creating different versions of the artificial intelligence health support for all of the different people and/or different needs. When supporting new people and/or new needs, and/or supporting changed people and/or changed needs, entire new versions of the artificial intelligence health support may need to be created. In addition to this effort, the effort required to configure the artificial intelligence health support and the lack of flexibility may further contribute to lack of coherency in artificial intelligence conversations, perceived lack of competence, and so on.

The present disclosure relates to systems, methods, apparatuses, and computer program products for providing artificial intelligence health support for people. Specific, targeted treatments for people may be rendered by using a flow engine to call one or more conversational services. The specific, targeted treatments for the people may be tracked. The flow engine and/or one or more of the conversational services may include different instructions to perform for different programs and/or goals that have been configured for people. The flow engine and/or one or more of the conversational services may also include instructions to perform when certain features are active (which may be activated when certain programs and/or goals are configured for people), when data regarding activity for people are received, and so on. Other conversational services may be dedicated to particular programs and/or goals. Some conversational services may determine whether or not to perform various instructions repetitiously, such as determining not to perform such instructions repetitiously when a priority of a previous instruction is below a threshold.

In this context, programs may be overarching courses of treatment or actions for a person, designed to help with one or more conditions. Conditions may be health aspects that a person may address through the artificial intelligence health support, such as disease states and/or other types of health statuses. The goals may define sets of features that each collectively define a targeted treatment (which may be activated when the goals are activated) that helps serve an aim that a person may pursue via one or more of the programs, which may generally result in treating, alleviating, or helping with a condition. Features may be conversational modules and/or other modules and/or system components that may be customizable and/or configurable to perform various interactions with the person and/or other people, devices, and so on. In some cases, features may provide the person one or more tasks that may be undertaken to accomplish one or more aims associated with one or more goals, within the framework of one or more programs. In other cases, features may perform various actions and/or enable the people to perform various such actions, such as food logging, enabling the people to log food, setting one or more reminders to measure blood glucose (such as in relation to an expected and/or past event like an expected and/or most recent meal and/or any other event), enabling people to set one or more reminders to measure blood glucose, setting one or more reminders for people to log their weight using a connected scale, enabling people to set one or more reminders for people to log their weight using a connected scale, enabling the people to use other devices (such as a wearable device, a scale, a fitness monitor, and so on) with the app and/or application, enabling the people to initiate one or more particular conversations, initiating one or more particular conversations, and/or various other actions. The missions may be curated clinical content that may be served in a gamified manner. The missions may be a type of feature. The missions may be discrete as compared to other features that may be more open ended, and may provide feedback to a person regarding his progress toward one or more programs, goals, and so on.

This structure of the flow engine and the conversational services may enable a great deal of flexibility in providing artificial intelligence health support for the people that renders specific, targeted treatment for the people and tracks those treatments because different programs can be configured differently for people with different goals and/or different missions without having to generate and store completely different flow engines and/or conversational services for each. Being able to select one or more of the multiple interoperable programs for a person and configure it with one or more goals and/or one or more missions in a way that is usable with the flow engine and at least some of the conversational services to provide artificial intelligence health support for the person that renders specific, targeted treatment for the person and tracks that treatment may reduce the time and effort necessary to configure the artificial intelligence health support, as well as improve the operation of components of electronic devices and/or systems that implement the flow engine, conversational services, programs, goals, and/or missions and/or provide the artificial intelligence health support due to the fewer hardware and/or software resources (such as memory, processing resources, storage space, and so on) necessary to store and/or execute the flow engine and/or the conversational services or modules. The flow engine, the conversational services, and their interactions are discussed in more detail below.

These and other embodiments are discussed below with reference to FIGS. 1-9. However, those skilled in the art will readily appreciate that the detailed description given herein with respect to these Figures is for explanatory purposes only and should not be construed as limiting.

FIG. 1 depicts an example system 100 for providing artificial intelligence health support for people that renders specific, targeted treatment for the people and tracks those treatments. The system 100 may include one or more backend processes 106, provided via one or more servers 104 and/or databases 118, that people may interact with via one or more apps or applications executing on one or more user devices 102. The backend process 106 may provide artificial intelligence health support for people that the people may interact with via the user device 102. That artificial intelligence health support may render specific, targeted treatment for the people and track those treatments.

For example, people may provide input associated with the artificial intelligence health support to and/or receive output associated with the artificial intelligence health support from the backend process 106 and/or the server 104 and/or the database 118 via the user device 102. Similarly, the backend process 106 and/or the server 104 and/or the database 118 may receive input associated with the artificial intelligence health support from and/or provide output associated with the artificial intelligence health support to people via the user device 102.

The backend process 106 may support a number of programs 108, goals 110, and missions 112 as part of providing the artificial intelligence health support. Instructions executable by one or more processing units, computer code, data, and/or other information for such programs 108, goals 110, and missions 112 may be stored by the server 104, the database 118, the user device 102, and/or otherwise stored. In this context, the programs 108 may be overarching courses of treatment or actions for a person, designed to help with one or more conditions. Conditions may be health aspects that a person may address through use of the system 100, such as disease states and/or other types of health statuses. The goals 110 may define sets of features that each collectively define a targeted treatment that helps serve an aim that a person may pursue via one or more of the programs 108, which may generally result in treating, alleviating, or helping with a condition. Features may be conversational modules 114 and/or other modules and/or system 100 components that may be customizable and/or configurable to perform various interactions with the person and/or other people, devices, and so on. In some cases, features may provide the person one or more tasks that may be undertaken to accomplish one or more aims associated with one or more goals 110, within the framework of one or more programs 108. The missions 112 may be curated clinical content that may be served in a gamified manner. The missions 112 may be a type of feature. The missions 112 may be discrete as compared to other features that may be more open ended, and may provide feedback to a person regarding his progress toward one or more programs 108, goals 110, and so on.

Examples of the programs 108 may include diabetes management or care, diabetes prevention, hypertension management or care, hypertension prevention, weight loss, behavioral health, coronary artery disease/high cholesterol, chronic obstructive pulmonary disease, asthma, comorbidities (such as a combination of hypertension and diabetes, which may involve adjusting features and/or other system 100, such as one or more nutritional thresholds, differently than is used for separate hypertension and diabetes programs 108), congestive heart failure, cardiac rehab, and so on. A diabetes management or care program 108 may help people gain better control of their diabetes through blood glucose measurement and coaching; diabetes-specific digital nutritional therapy; diabetes educational content; personalized coaching on weight loss, activity, stress, and sleep; and so on. A diabetes prevention program 108 may help people with diabetes prevent the progression to type 2 diabetes through personalized coaching. A hypertension management or care program 108 may help people attain controlled blood pressure through blood pressure measurement and coaching; hypertension-specific digital nutritional therapy; hypertension educational content; personalized coaching on weight loss, activity, stress, and sleep, and so on. A behavioral health program 108 may focus on helping people improve their health and prevent future chronic disease by providing personalized coaching to address behavioral health issues, such as anxiety and stress, quitting tobacco, losing weight, and so on. Information for the programs 108 may be stored in the user progress 120.

Examples of tasks that may be provided by one or more features may include performing a weight check undertaken to accomplish a weight loss goal 110, performing a glucose test undertaken to accomplish a lower glucose goal 110, going for a walk undertaken to accomplish a weight loss goal 110, meditating undertaken to accomplish a lower blood pressure goal 110, avoiding exceeding daily recommended carbohydrates undertaken to accomplish a weight loss goal 110, performing positive affirmations undertaken to accomplish an improve mood goal 110, staying within a daily calorie allowance undertaken to accomplish a weight loss goal 110, and so on.

Examples of missions 112 may include curated clinical content providing education about weight loss, lowering glucose, methods of exercise, meditation, dietary suggestions, and so on. Outstanding and/or tasks completed missions 112, tasks, and/or goals 110 may be tracked in the user progress 120.

Examples of features may include conversational modules 114, mood check-ins, other actions that the background process 106 and/or the system 100 may perform, and so on. By way of illustration, a feature may determine that the person is not doing well and may notify a third party and/or device, such as when the feature determines that the person needs immediate medical attention.

The programs 108 may be configured for people with one or more of the goals 110 and/or one or more of the missions 112. The missions 112 for which the programs 108 may be configured for the people may be associated with one or more of the goals 110 for which the programs have been configured for the people. One or more of the goals 110 and/or the missions 112 may correlate to multiple different programs 108. Similarly, the missions 112 may correlate to multiple different goals 110. Such configurations may be specified by configuring user information that is stored in the user progress 120.

In various embodiments, a particular mission 112 may only be associated with one goal 110 for a particular person. However, that same particular mission 112 may be assigned to different goals 110 for different people. This may enable the same clinical content to be used for different people configured with different programs 108 and/or different goals 110. Various configurations are possible and contemplated without departing from the scope of the present disclosure.

The goals 110 may be configured by priority and focus. By way of example, some features related to one or more goals 110 may be shown before others. By way of another example, some goals 110 may take up a greater percentage of the user interface of the system 100 than others. By way of illustration, the goals 110 may be configured as primary or secondary for one or more of the programs 108. In such an implementation, primary and secondary may function as nomenclature for priority and focus. The backend process 106 may behave differently with respect to the goals 110 when the goals are configured as primary than when the goals 110 are configured as secondary. The goals 110 may be required or optional for various of the different programs 108. Some of the goals 110 may be required for some of the programs 108 and optional for other of the programs 108. In various embodiments, the programs 108 may be configured with the missions 112 that are associated with one of the goals 110 that has been configured as primary. In other examples, the programs may be configured with missions 112 that are associated with multiple of the goals 110 and logic may be included to prevent conflicts among the missions 112, to present a certain number of missions 112 associated with a set of highest ranked of the goals 110, and so on.

This structure of the multiple interoperable programs 108, goals 110, and missions 112 may enable a great deal of flexibility in providing artificial intelligence health support for the people that renders specific, targeted treatment for the people and tracks those treatments because different programs 108 can be configured for people with different goals 110 and/or different missions 112 without having to generate and store completely different programs 108, goals 110, and/or missions 112 for each. Being able to select one of the multiple interoperable programs 108 for a person and configure it with one or more goals 110 and/or one or more missions 112 to provide artificial intelligence health support for the person that renders specific, targeted treatment for the person and tracks that treatment may reduce the time and effort necessary to configure the artificial intelligence health support, as well as improve the operation of the server 104, the database 118, and/or the system 100 due to the fewer hardware and/or software resources (such as memory, processing resources, storage space, and so on) necessary to store and/or execute the programs 108, the goals 110, and/or the missions 112. The programs 108, the goals 110, the missions 112, and their interactions are discussed in more detail below.

The backend process 106 may also support one or more flow engines 116 and/or one or more conversational modules 114. Instructions executable by one or more processing units, computer code, data, and/or other information for such a flow engine 116 and/or such conversational modules 114 may be stored by the server 104, the database 118, the user device 102, and/or otherwise stored. The flow engine 116 may be implemented using a decision tree, priority queue, and/or other static or dynamic data structure or component, such as artificial intelligence, machine learning, and so on. The flow engine 116 may include a series of decision nodes and/or action nodes that the backend process 106 may proceed through as part of providing the artificial intelligence health support. Such decision nodes may gate to one or more action nodes and/or other decision nodes using logic, algorithms, heuristics, data, artificial intelligence, and/or machine learning according to the occurrence of various events, the program 108 that is configured for a person, one or more of the goals 110 that are configured for the person, whether one or more of the goals 110 that are configured for the person are primary or secondary, whether one or more of the goals 110 that are configured for the person are required or optional, whether one or more features are active (which may be activated according to the program 108 that is configured for the person, one or more of the goals 110 that are configured for the person, and so on), actions the person has taken, received data for the person, and so on. Such action nodes may perform various actions and/or call one or more of the conversational modules 114.

The flow engine 116 may include various structures for interrupting and/or ending the flow. For example, such structures may be used to interrupt and/or end the flow upon determining that the person has been provided sufficient interaction to prevent the person from being overwhelmed, upon determining that the priority of the last action exceeds a threshold so that the last action will be emphasized to the person, and so on. Such structures may include recursive calls, repetitive sections of instructions, and/or other structures that may be exited to interrupt and/or end the flow.

The conversational modules 114 may enable people to engage in a back-and-forth conversation with the backend process 106. This back-and-forth conversation may enable the people and/or the backend process 106 to give and receive details and directives pertaining to the associated programs 108, goals 110, missions 112, features, wellness habits, user actions, user needs, user interests, user questions, empathy, and so on. Some conversational modules 114 may be dedicated to particular programs 108, goals 110, features, or missions 112. Other conversational modules 114 may be usable with multiple programs 108, goals 110, features, or missions 112, such as by including decision points that are gated to different instructions or computer code using logic, algorithms, heuristics, data, artificial intelligence, and/or machine learning according to the occurrence of various events, the program 108 that is configured for a person, one or more of the goals 110 that are configured for the person, whether one or more of the goals 110 that are configured for the person are primary or secondary, whether one or more of the goals 110 that are configured for the person are required or optional, whether one or more features are active (which may be activated according to the program 108 that is configured for the person, one or more of the goals 110 that are configured for the person, and so on), actions the person has taken, received data for the person, and so on.

The backend process 106 may instantiate one or more services that may execute and/or otherwise use one or more of the conversational modules 114. A service may be a process and/or processing thread instantiated by one or more server allocations (such as the server 104) that performs one or more operations on behalf of one or more clients (such as the user device 102). Although specific named services are discussed herein, it is understood that these are examples and any number of different structures of a service and/or services may be used to implement such functions. By way of illustration, an onboarding service may execute and/or otherwise use an onboarding conversational module 114, a glucose level service may execute and/or otherwise use a glucose level conversational module 114, a weight conversation service may execute and/or otherwise use a weight conversational module 114, a diet monitoring service that may execute and/or otherwise use a diet monitoring conversational module 114, a mental check-in service that may execute and/or otherwise use a mental check-in conversational module 114, a goal completion service may execute and/or otherwise use a goal completion conversational module 114, an artificial intelligence health support service may execute and/or otherwise use artificial intelligence health support conversational module 114, and so on. By way of another illustration, a single service may execute and/or otherwise use multiple conversational modules 114, such as a glucose level service that executes and/or otherwise uses a glucose level conversational module 114, a weight conversational module 114, and/or a diet monitoring conversational module 114. In yet another illustration, a single service may use all conversational modules 114 and/or perform all functions associated with the backend process 106. Various configurations are possible and contemplated without departing from the scope of the present disclosure.

In various examples, the system 100 may include an intention engine that may be used to process inputs from a person. Such an intention engine may analyze text input to parse semantic meaning, such as by determining maximum probabilities of particular intentions. By way of illustration, a diet monitoring service may receive an input that a person had a burger with tomatoes and fries for lunch. The diet monitoring service may use the intention engine to determine that the person most probably intended to say that the person had a slice of tomato on a burger as well as fries rather than a burger, a whole tomato, and fries. Various configurations are possible and contemplated without departing from the scope of the present disclosure.

The following is an example conversation that may be performed between a person and a diet monitoring service:

Diet Monitoring Service: What did you eat today?
Person: A burger with tomato and fries.

Diet Monitoring Service: Great! You stayed under your 650 calorie goal for the meal. Way to go!

The conversational modules 114 may be adaptive and/or otherwise context dependent. In other words, the conversational modules 114 may behave differently depending on the context in which the conversational modules 114 are called. This may be used to improve the coherency of the associated conversation, minimize the shock and/or confusion of switching to the conversational module 114 from a previous activity and/or action, improve the flexibility of the conversational module 114, and so on.

By way of example, some of the conversational modules 114 may behave differently depending on the time of day in which they are called. Such different behaviors may involve different entry language, different multiple conversation thread possibilities that may be selected among, and so on. A diet monitoring module may ask if a person has eaten a meal when called around mealtimes and ask when the last time was that a person ate when called at other times. Various configurations are possible and contemplated without departing from the scope of the present disclosure.

By way of another example, some of the conversational modules 114 may behave differently depending upon receipt of particular data points. A weight loss module may present analysis of weight loss progress when a recent weight for the person has been received and weight loss tutorial when recent weight for the person has not been received. Various configurations are possible and contemplated without departing from the scope of the present disclosure.

In another example, some of the conversational modules 114 may behave differently depending where they are called in the flow of providing artificial intelligence health support. A conversational module 114 may provide a longer conversation when called earlier in the flow of providing artificial intelligence health support and a shorter conversation when called later in the flow of providing artificial intelligence health support. Various configurations are possible and contemplated without departing from the scope of the present disclosure.

In still another example, some of the conversational modules 114 may use different entry language to provide different transitions depending on how related a previously performed action was. A conversational module 114 may provide a first transition using first entry language when called after performing a related action and a second transition using second entry language when called after performing an unrelated action. This may minimize the shock and/or confusion of switching to the conversational module 114 from the previously performed action when appropriate, while being able to omit and/or reduce performance of such when it may not be helpful. Various configurations are possible and contemplated without departing from the scope of the present disclosure.

This structure of the flow engine 116 and the conversational modules 114 may enable a great deal of flexibility in providing artificial intelligence health support for the people that renders specific, targeted treatment for the people and tracks those treatments because different programs 108 can be configured differently for people with different goals 110 and/or different missions 112 without having to generate and store completely different flow engines 116 and/or conversational modules 114 for each. Being able to select one of the multiple interoperable programs 108 for a person and configure it with one or more goals 110 and/or one or more missions 112 in a way that is usable with the flow engine 116 and at least some of the conversational modules 114 to provide artificial intelligence health support for the person that renders specific, targeted treatment for the person and tracks that treatment may reduce the time and effort necessary to configure the artificial intelligence health support, as well as improve the operation of the server 104, the database 118, and/or the system 100 due to the fewer hardware and/or software resources (such as memory, processing resources, storage space, and so on) necessary to store and/or execute the flow engine 116 and/or the conversational modules 114. The flow engine 116, the conversational modules 114, and their interactions are discussed in more detail below.

As described above, the system 100 may provide artificial intelligence health support for people that renders specific, targeted treatment for the people and tracks those treatments. By way of an example, the system 100 may provide artificial intelligence health support for a people configured with a diabetes treatment program 108 that renders specific, targeted treatment for that person and tracks that treatment. For example, the specific, targeted treatment may monitor the person's glucose level, provide education about dietary changes that will reduce the person's glucose level via one or more conversational modules 114, reorder glucose test strips and insulin for the person, remind the person to test the person's glucose, remind the person to take the person's insulin when the person's glucose level is high, and so on. The specific, targeted treatment may be tracked to determine the person's performance lowering the person's glucose, adjust the specific, targeted treatment based on the tracking, notify one or more medical providers regarding the person's performance lowering the person's glucose, summon assistance if the person's glucose level reaches dangerous levels, and so on. Various configurations are possible and contemplated without departing from the scope of the present disclosure.

As illustrated, the database 118 may store data related to user progress 120 for one or more people. The user progress 120 may be data associated with the system 100 providing artificial intelligence health support for the people that renders specific, targeted treatment for the people and tracks those treatments. The data may relate to progress of one or more people towards one or more of the programs 108, the goals 110, the missions 112, and so on. The data may include state data regarding the people monitored by the user device 102 and/or one or more other devices (such as one or more fitness monitors; accelerometers; motion detectors; odometers; scales; and/or any medical, fitness, or other health-related device; and so on). By way of illustration, the user progress 120 may receive and store data associated with activity of the people, fitness actions performed by the people, heart rate and/or other monitored health information for the people, health-related tests performed by medical professionals and/or other, dietary records associated with the people, and/or other information related to progress of one or more people towards one or more of the programs 108, the goals 110, the missions 112, and so on. The data may also include user information specifying one or more of the programs 108, the goals 110, the missions 112, and so on that have been configured for one or more people.

The database 118 may include one or more data structures accessible by the server 104, the backend process 106, the user device 102, and so on that may store data related to the user progress 120, the programs 108, the goals 110, the missions 112, the conversational modules 114, the flow engine 116, and so on. Such data structures may include one or more ordered and/or unordered arrays, stacks, queues, tables, lists, and so on. Various configurations are possible and contemplated without departing from the scope of the present disclosure.

The app or application executing on the user device 102 may perform a variety of different functions. By way of example, the app or application executing on the user device 102 may receive various kinds of input from one or more people, the user device 102 itself, and/or other connected devices (such as one or more glucose monitors, wearable devices, and so on) and provide the input to the server 104, the background process 106, the database 118, another device, and so on. Such input may drive various actions performed by the backend process 106, such as where the input drives artificial intelligence or machine learning performed by the backend process 106. Such input may drive various actions performed by third parties, such as where the input requests materials or other actions from third parties (such as ordering glucose strips; ordering medication; care escalation functions upon the occurrence of conditions like blood sugar spikes, irregular heart activity during monitored sleep, and so on).

The app or application executing on the user device 102 may also provide various kinds of output using data received from the server 104, the background process 106, the database 118, another device, and so on. Such output may include text, pop up reminders, graphs relating to a person's progress and/or other data, video, and so on.

Additionally, the app or application executing on the user device 102 may perform one or more of the various functions attributed elsewhere herein to the server 104, the background process 106, the database 118, another device, and so on. For example, the system 100 may weigh various factors (such as a delay associated with communicating with the server 104, responsiveness associated with local processing, cost associated with the server 104, and so on) in having the app or application, the server 104, the background process 106, the database 118, another device, and so on perform one or more functions and assign performance of the function accordingly.

The user device 102 may be any kind of electronic device and/or cloud and/or other computing arrangement. Examples of such devices include, but are not limited to, one or more desktop computing devices, laptop computing devices, mobile computing devices, wearable devices, tablet computing devices, mobile telephones, kiosks and/or other stations, smart phones, printers, displays, vehicles, kitchen appliances, entertainment system devices, digital media players, cloud computing and/or other cooperative computing arrangements, and so on. The user device 102 may include one or more processors and/or other processing units or controllers, communication units, non-transitory storage media, and/or other components. The processor may execute one or more sets of instructions stored in the non-transitory storage media to perform various functions, such as receiving input from one or more people; providing the input to the server 104, the backend process 106, and/or the database 118; receiving output from the server 104, the backend process 106, and/or the database 118; providing the output to the one or more people; and so on.

Similarly, the server 104 may be any kind of electronic device and/or group of electronic devices (such as one or more cloud computing and/or other cooperative computing arrangements). The server 104 may include one or more processors and/or other processing units and/or controllers, one or more non-transitory storage media (which may take the form of, but is not limited to, a magnetic storage medium; optical storage medium; magneto-optical storage medium; read only memory; random access memory; erasable programmable memory; flash memory; and so on), one or more communication units; and/or one or more other components. The processor may execute one or more sets of instructions stored in the non-transitory storage media to perform various functions, such as providing artificial intelligence health support for people that renders specific, targeted treatment for the people and tracks those treatments, communicating with the user device 102 and/or the database 118; executing the background process; and so on. Alternatively and/or additionally, the server 104 may involve one or more memory allocations configured to store at least one executable asset and one or more processor allocations configured to access the one or more memory allocations and execute the at least one executable asset to instantiate one or more processes and/or services, such as the backend process 106, an onboarding service, a glucose level service, a weight conversation service, a diet monitoring service may that execute and/or otherwise use a diet monitoring conversational module 114, a mental check-in service that may execute and/or otherwise use a mental check-in conversational module 114, a goal completion service that may execute and/or otherwise use a goal completion conversational module 114, an artificial intelligence health support service, and so on.

The system 100 may store, interact with, and/or otherwise access information associated with people that may need to be kept private and/or otherwise protected. This may include personally identifying information, health related information, and so on. As such, the system 100 may include encryption, data separation and/or other techniques to securely keep data associated with different people distinct and different. In some examples, data may be permitted to be shared with affiliated parties (such as insurers, medical professionals, and so on) and such encryption, data separation and/or other techniques may be used to securely share access to such data with permitted affiliated parties to the extent that such sharing is permitted for such affiliated parties. In various examples, the encryption scheme used with one person and/or affiliated party may be different from the encryption scheme used with another person and/or affiliated party. This may ensure that accidental data access between people and/or affiliated parties does not occur. Various configurations are possible and contemplated without departing from the scope of the present disclosure.

Although the system 100 is illustrated and described as including a specific arrangement of specific components, it is understood that this is an example. In other implementations, other arrangements of the same, similar, and/or different components may be used without departing from the scope of the present disclosure.

For example, the above is illustrated and described as using the missions 112 associated with one of the goals 110 when that one of the goals 110 is primary but not when that one of the goals 110 is secondary. However, in other examples, the missions 112 associated with one of the goals 110 may be used regardless whether that one of the goals 110 is primary or secondary, such as when that one of the goals 110 is required but not when that one of the goals 110 is optional or regardless whether that one of the goals 110 is required or optional. In such examples, conflicts between various of the missions 112 associated with different ones of the goals 110 may be resolved in various ways, such as according to a priority of the associated goal 110. By way of illustration, goals 110 configured as primary may have a higher priority than goals configured as secondary, and goals 110 configured as required may have a higher priority than goals 110 configured as optional. Various configurations are possible and contemplated without departing from the scope of the present disclosure.

By way of another example, the above is illustrated and described as using the missions 112 associated with one of the goals 110. However, in other examples, various of the missions 112 may be used according to an association between those of the missions 112 and one or more of the programs 108. Various configurations are possible and contemplated without departing from the scope of the present disclosure.

In yet another example, the above is illustrated and described as the database 118 being separate from the server 104. However, it is understood that this is an example. In various implementations, the database 118 may be a component of the server 104 and/or otherwise associated with the server. Various configurations are possible and contemplated without departing from the scope of the present disclosure.

By way of yet another example, the user device 102 is not illustrated as communicably connected to the database 118 the way that the server 104 is. However, it is understood that this is an example. In various implementations, the user device 102 may be communicably connected to the database 118 in the way as the server 104. Various configurations are possible and contemplated without departing from the scope of the present disclosure.

In still another example, the above illustrates and describes the backend process 106 as being provided via one or more servers 104 and/or databases 118. However, it is understood that this is an example. In various implementations, at least some functions attributed to the backend process 106 may be performed by the user device 102. Various configurations are possible and contemplated without departing from the scope of the present disclosure.

In yet another example, the above illustrates and describes multiple of the programs 108, the goals 110, and the missions 112. However, it is understood that this is an example. In various implementations, some of the multiple versions of the programs 108, the goals 110, and/or the missions 112 may be omitted. By way of illustration, in some implementations, a single program 108 may be included that may be configured with multiple different of the goals 110 and/or the missions 112. By way of another illustration, in some implementations, one or more of the programs 108 may be used with one or more of the goals 110 without any of the missions 112. Various configurations are possible and contemplated without departing from the present disclosure.

In still another example, the above illustrates and describes configuration of a single programs 108 for a person. However, it is understood that this is an example. In various implementations, multiple programs 108 may be configured for a person. In such implementations, various techniques may be used to handle conflicts between the programs, such as blocking advice provided for one of the programs 108 that is contrary to the other program 108, such as by preventing a weight loss program 108 from providing advice regarding reduced calorie intake and instead providing advice regarding balanced diet, exercise, and so on when the person is also configured for an anorexia treatment program 108. Various configurations are possible and contemplated without departing from the present disclosure.

In yet another example, the above illustrates and describes providing artificial intelligence health support to individual people. However, it is understood that this is an example. In various implementations, actions may be performed related to one or more groups of people. For example, data regarding artificial intelligence health support provided to multiple people may be retrieved, aggregated, anonymized, and/or analyzed. This may trigger one or more interventions and/or other actions that may drive artificial intelligence and/or other functions performed by the backend process 106. Such interventions and/or other actions may involve communicating with one or more third parties based on the data retrieved, aggregated, anonymized, and/or analyzed. Various configurations are possible and contemplated without departing from the present disclosure.

The above illustrates and describes use of the programs 108, the goals 110, and the missions 112. However, it is understood that this is an example. In various implementations, one or more of the programs 108, the goals 110, and/or the missions 112 may be omitted. By way of illustration, in some implementations, the missions 112 may be omitted. Various configurations are possible and contemplated without departing from the present disclosure.

Figure 2A:
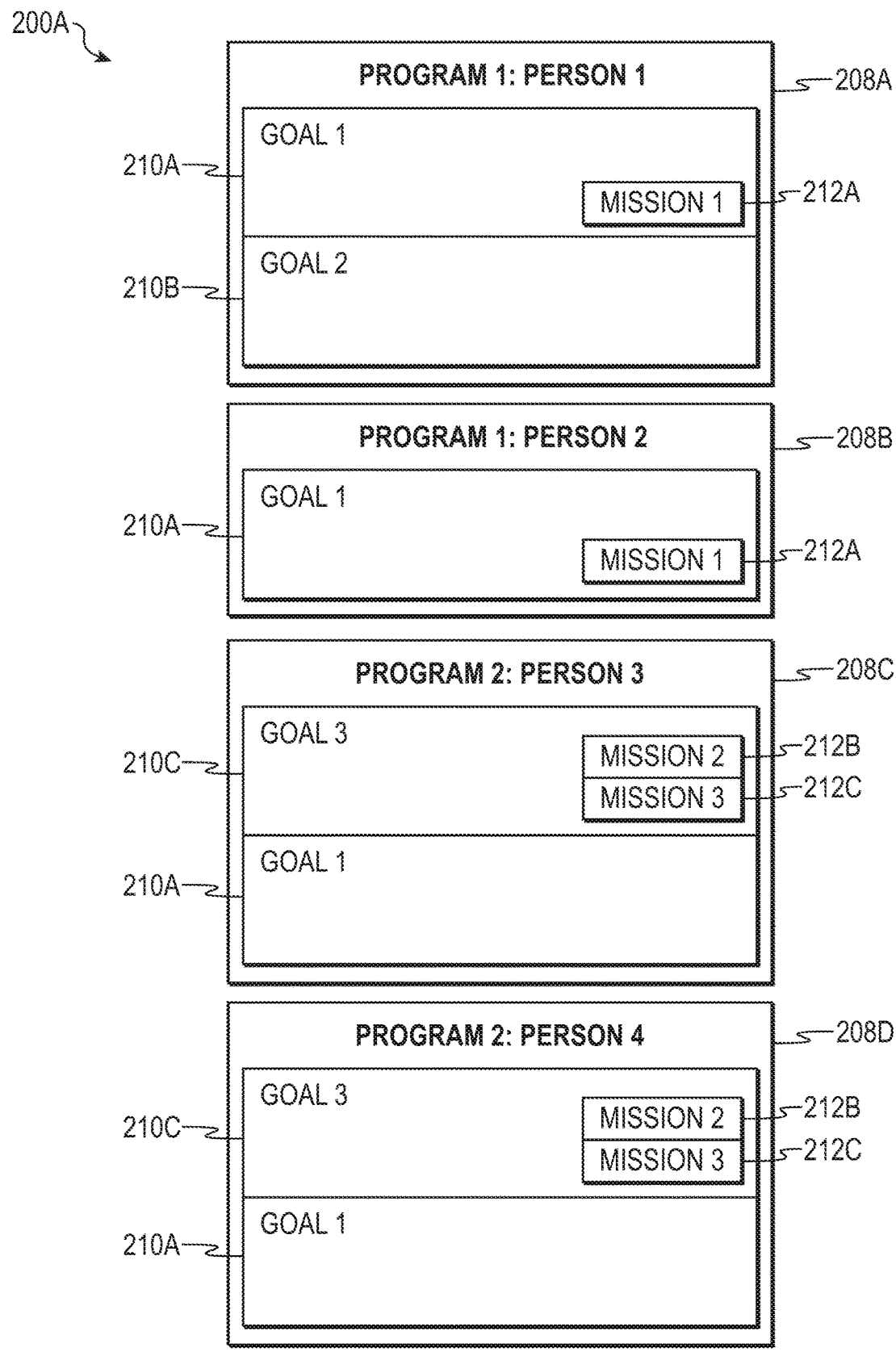
FIG. 2A depicts a first example set of programs configured for one or more people with one or more goals and missions. This example set of programs may be used with the system of FIG. 1.

FIG. 2A depicts an example set of programs 200A configured for one or more people with one or more goals and missions. This example set of programs 200A may be used with the system 100 of FIG. 1.

This example set of programs 200A includes programs 208A-208D. The program 208A is a first program configured for a first person. The program 208B is the first program configured for a second person. The program 208C is a second program configured for a third person. The program 208D is the second program configured for a fourth person.

The programs 208A and 208B are both configured with a first goal 210A, which is configured with a first mission 212A. The programs 208C and 208D are also configured with the first goal 210A, but the first goal 210A for the programs 208C and 208D is not configured with the first mission 212A. This illustrates that the same goal may be used for multiple programs, though the same goal may be configured differently for different programs (such as with or without missions).

The program 208A is also configured with a second goal 210B, which is not configured with any missions. However, the program 208B is not configured with the second goal 210B. This illustrates that the same program may be configured for different people with different goals and/or different missions.

The programs 208C and 208D are both configured with a third goal 210C. The third goal 210C is configured with a second mission 212B and a third mission 212C for both of the programs 208C and 208D. This illustrates that a program may be configured for two different people in a way that results in the respective configured programs for the respective people being the same.

However, it is understood that this is an example. In various implementations, various programs, goals, missions, and so on may be configured in a variety of different ways for a variety of different people. Various configurations are possible and contemplated without departing from the scope of the present disclosure.

Figure 2B:
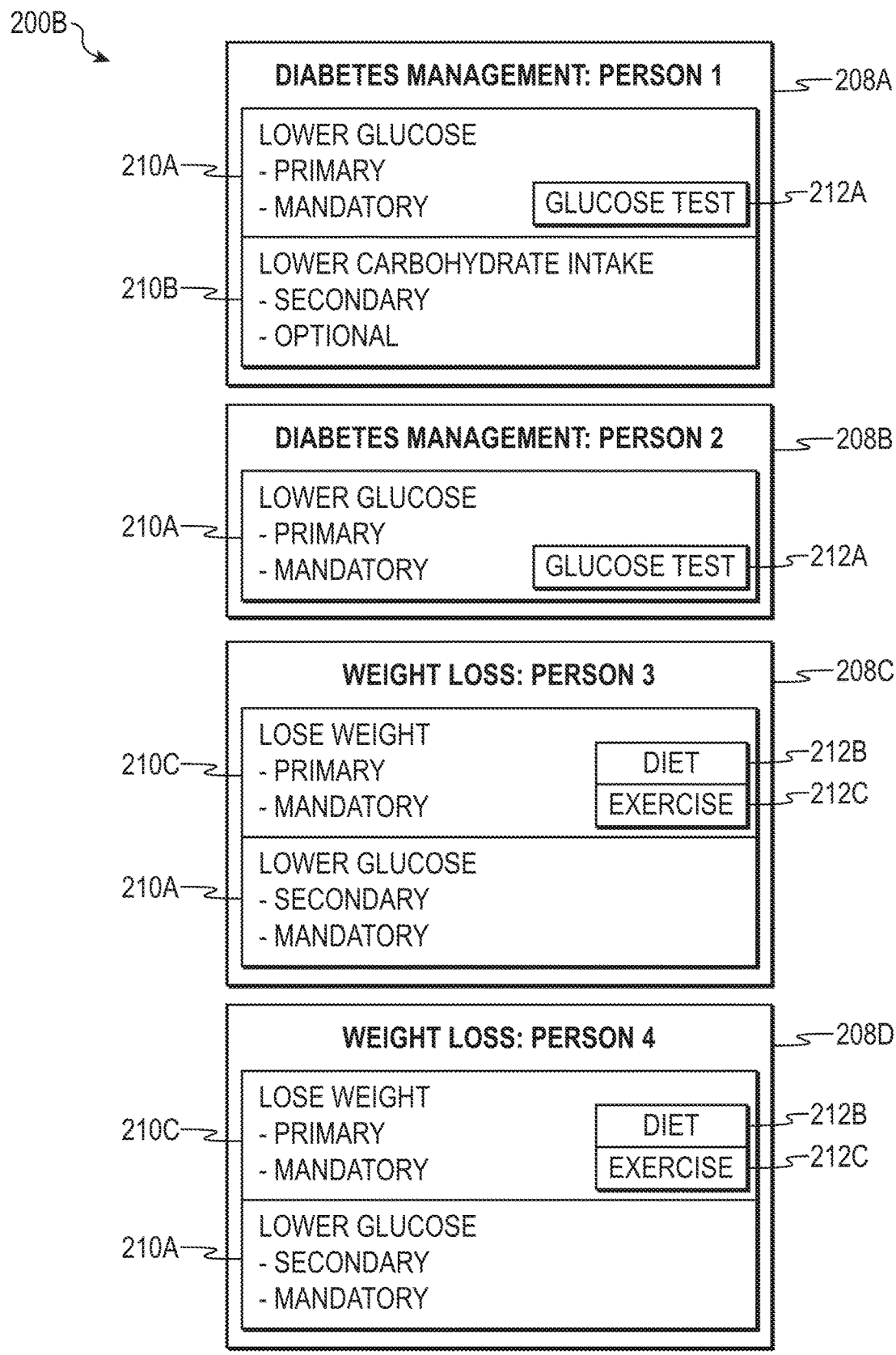
FIG. 2B depicts a more detailed version of the example set of programs configured for one or more people with one or more goals and missions of FIG. 2A.

FIG. 2B depicts a more detailed version 200B of the example set of programs 200A configured for one or more people with one or more goals and missions of FIG. 2A. In this more detailed version 200B, the first program may be a diabetes management (or care) program and the second program may be a weight loss program.

Further, in this more detailed version 200B, the first goal 210A may be a set of features that collectively define a targeted treatment that helps serve an aim of lowering glucose, the second goal 210B may be a set of features that collectively define a targeted treatment that helps serve an aim of lowering carbohydrate intake, and the third goal 210C may be a set of features that collectively define a targeted treatment that helps serve an aim of losing weight.

In this example, the set of features that collectively define a targeted treatment that helps serve an aim of lowering glucose is primary and mandatory for the diabetes management (or care) program, but secondary and mandatory for the weight loss program. Further in this example, the set of features that collectively define a targeted treatment that helps serve an aim of lowering carbohydrate intake is secondary and optional for the diabetes management (or care) program. Additionally in this example, the set of features that collectively define a targeted treatment that helps serve an aim of losing weight is primary and mandatory for the weight loss program.

Moreover, in this more detailed version 200B, the first mission 212A is curated clinical content relating to glucose tests that may be served in a gamified manner. Further, in this more detailed version 200B, the second mission 212B is curated clinical content relating to diet/dietary modifications that may be served in a gamified manner, and the third mission 212C is curated clinical content relating to exercise that may be served in a gamified manner.

However, it is understood that this is an example. In various implementations, the first program and the second program may be a variety of different programs; the first goal 210A, the second goal 210B, and the third goal 210C may be a variety of different goals; and the first mission 212A, the second mission 212B, and the third mission 212C may be a variety of different missions. Various configurations are possible and contemplated without departing from the scope of the present disclosure.

Figure 3:
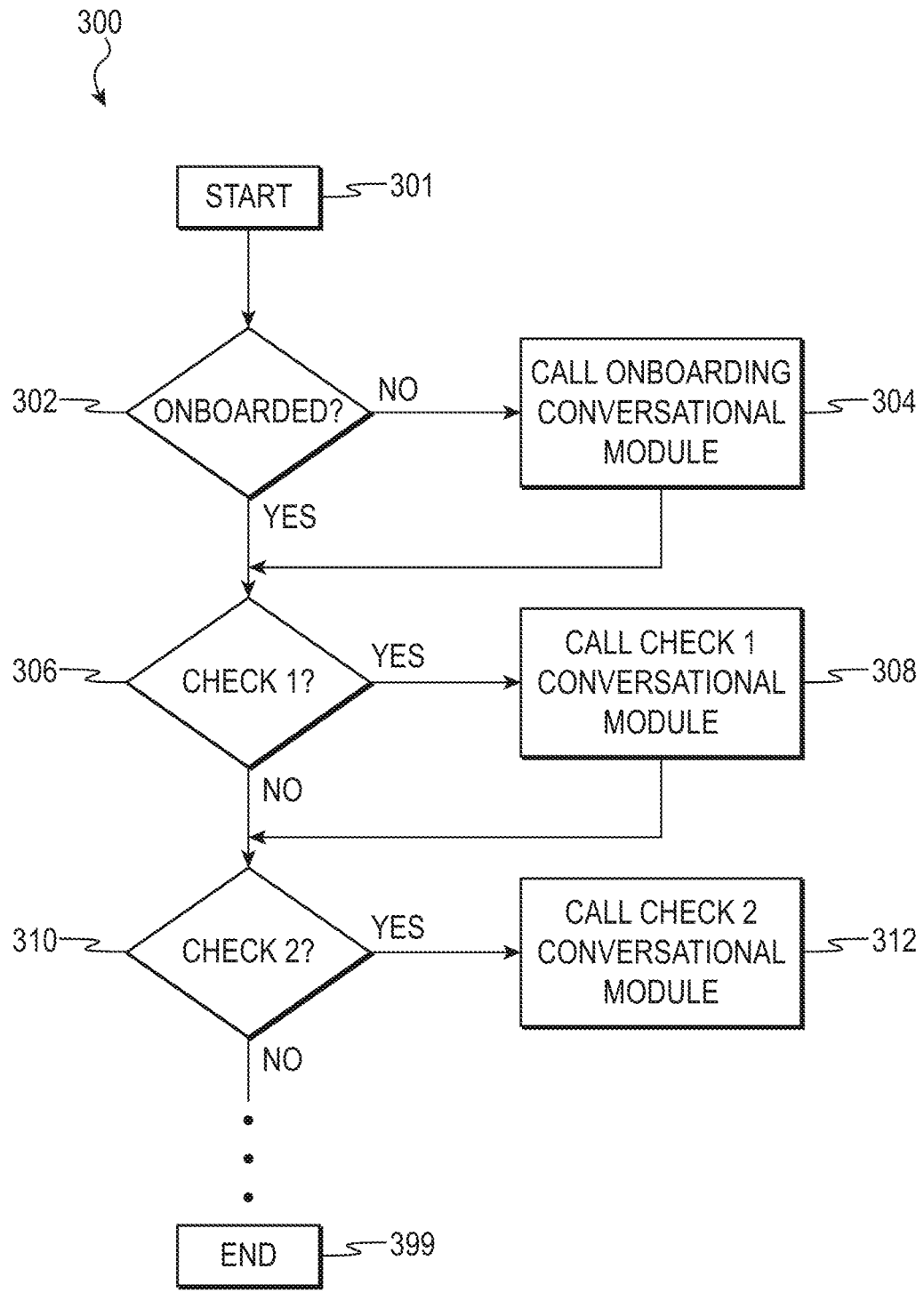
FIG. 3 depicts an example flow engine. This example flow engine may be used with the system of FIG. 1.

FIG. 3 depicts an example flow engine 300. This example flow engine 300 may be used with the system 100 of FIG. 1.

As described above with respect to FIG. 1, the flow engine 300 includes a series of decision nodes (such as decision nodes 302, 306, and 310) and/or action nodes (such as action nodes 304, 308, and 312) that one or more backend processes may proceed through as part of providing artificial intelligence health support. These decision nodes may gate to one or more action nodes and/or other decision nodes using logic, algorithms, heuristics, data, artificial intelligence, and/or machine learning according to the occurrence of various events, a program that is configured for a person, one or more of goals that are configured for the person, whether one or more of the goals that are configured for the person are primary or secondary, whether one or more of the goals that are configured for the person are required or optional, whether one or more features are active (which may be activated according to the program that is configured for the person, one or more of the goals that are configured for the person, and so on), actions the person has taken, received data for the person, and so on. The action nodes may perform various actions and/or call one or more conversational modules.

By way of illustration, the flow engine 300 may start at an operation 301 and proceed to a decision node 302. At the decision node 302, the backend process may determine whether or not the person is already onboarded (e.g., whether or not one or more programs have already been configured for the person, with or without one or more goals and/or missions). If not, the flow may proceed to an action node 304 where the backend process may call an onboarding conversational module before the flow proceeds to a decision node 306. Otherwise, the flow may proceed directly to the decision node 306.

At the decision node 306, the backend process may determine whether or not the result of a first check (or "check one") is positive. The first check may be any kind of check. If the result is positive, the flow may proceed to an action node 308 where the backend process may call a check one conversational module before the flow proceeds to a decision node 310. Otherwise, the flow may proceed directly to the decision node 310.

At the decision node 310, the backend process may determine whether or not the result of a second check (or "check two") is positive. The second check may be any kind of check. If the result is positive, the flow may proceed to an action node 312 where the backend process may call a check two conversational module.

It is noted that the check two conversational module is not shown returning to a decision node subsequent to the decision node 310. Instead, the check two conversational module may call another conversational module and/or another decision node, action node, or other point in the flow engine 300. Various configurations are possible and contemplated without departing from the scope of the present disclosure.

Further, it is noted that operations connecting decision node 310 and an operation 399 in the flow engine 300 are not shown. Any number of operations, or no operations, may connect decision node 310 and the operation 399 in the flow engine 300. Various configurations are possible and contemplated without departing from the scope of the present disclosure.

Eventually, the flow may reach the operation 399 in the flow engine and end.

Although the flow engine 300 is illustrated and described as including a particular series of operations performed in a particular order, it is understood that this is an example. In any number of implementations, various orders of the same, similar, and/or different operations may be used without departing from the scope of the present disclosure.

For example, the decision node 302 and the action node 304 are illustrated and described as calling an onboarding conversational module if the person is not already onboarded. However, this is an example. In various implementations, onboarding may be performed by a separate process than the flow engine 300. Various configurations are possible and contemplated without departing from the scope of the present disclosure.

Further, the flow engine 300 is illustrated and described as including at least two checks. However, this is an example. In various implementations, the flow engine may include any number of checks, such as one or a hundred. Various configurations are possible and contemplated without departing from the scope of the present disclosure.

By way of another example, the flow engine is illustrated and described above as implemented using a decision tree. However, it is understood that this is an example. In various implementations, the flow engine may be implemented using another static or dynamic data structure or component, such as a priority queue, artificial intelligence, machine learning, and so on. By way of illustration, a set of decision nodes and/or action nodes may be assigned priorities and placed in a priority queue. One of the set may be removed from the priority queue and used as the next operation in the flow. At various times, one or more of the priorities may be reevaluated and the priority queue may be reordered. In this way, the flow may be dynamically determined as compared to the static flow of the decision tree described above. Various configurations are possible and contemplated without departing from the scope of the present disclosure.

Figure 4:
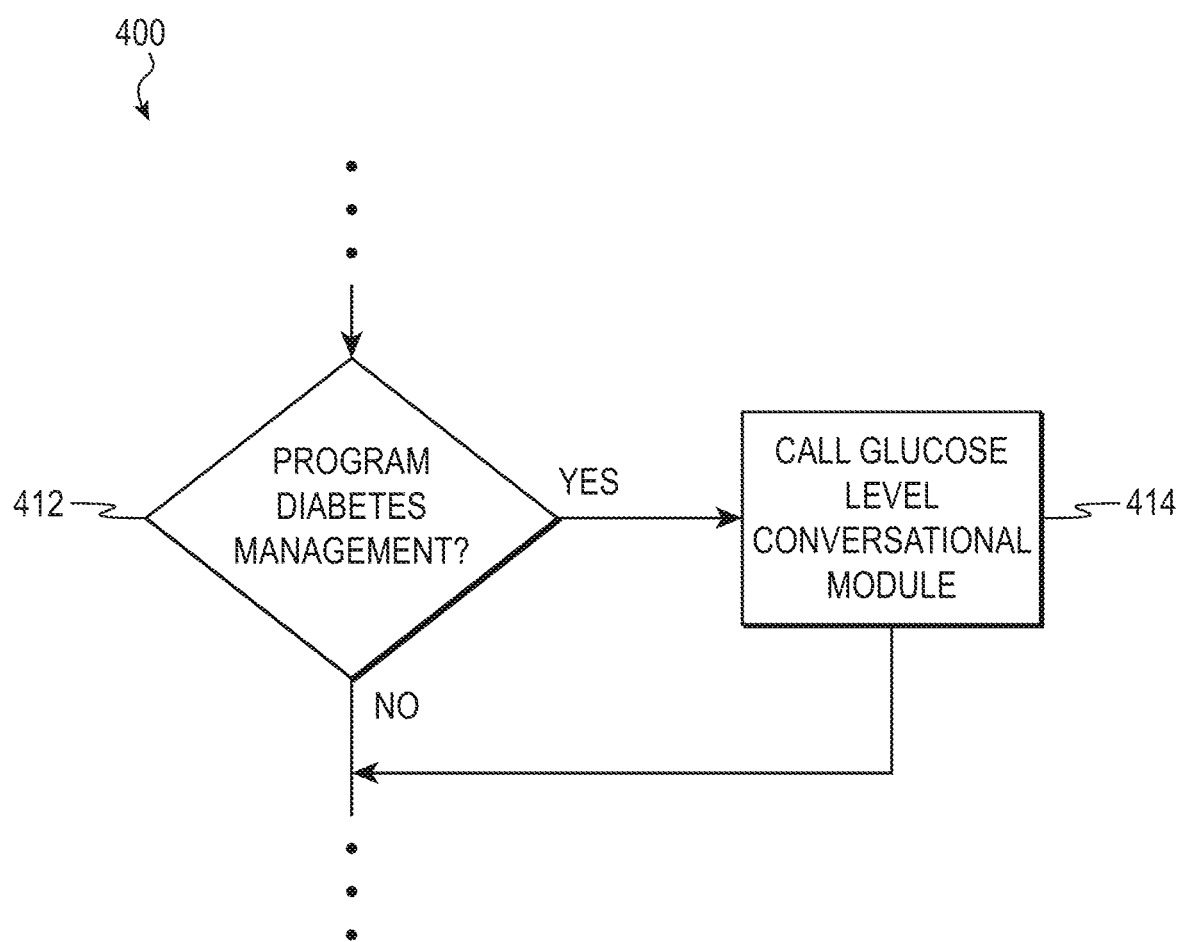
FIG. 4 depicts a first example decision block. This first example decision block may be used in a flow engine, such as the example flow engine of FIG. 3.

FIG. 4 depicts a first example decision block 400. This first example decision block 400 may be used in a flow engine, such as the example flow engine 300 of FIG. 3.

This first example decision block 400 includes a decision node 412. As described above with respect to FIG. 3, decision nodes may gate to one or more action nodes and/or other decision nodes using logic, algorithms, heuristics, data, artificial intelligence, and/or machine learning according to the occurrence of various events, a program that is configured for a person, one or more of goals that are configured for the person, whether one or more of the goals that are configured for the person are primary or secondary, whether one or more of the goals that are configured for the person are required or optional, whether one or more features are active (which may be activated according to the program that is configured for the person, one or more of the goals that are configured for the person, and so on), actions the person has taken, received data for the person, and so on.

In this example, the decision node 412 may be gated according to whether or not a person's goal is diabetes management (or care). If so, the flow may proceed to an action node 414 where one or more background processes may call a glucose level conversational module before the flow returns to a decision node, action node, and/or other point subsequent to the decision node 412. Otherwise, the flow may proceed directly to a decision node, action node, and/or other point subsequent to the decision node 412.

Although the first example decision block 400 is illustrated and described as including a particular series of operations performed in a particular order, it is understood that this is an example. In any number of implementations, various orders of the same, similar, and/or different operations may be used without departing from the scope of the present disclosure.

For example, the action node 414 is illustrated and described as calling the glucose level conversational module before the flow returns to a decision node, action node, and/or other point subsequent to the decision node 412. However, it is understood that this is an example. In other implementations, the background process may instead call a lower carbohydrate intake conversational module. Various configurations are possible and contemplated without departing from the scope of the present disclosure.

Figure 5A:
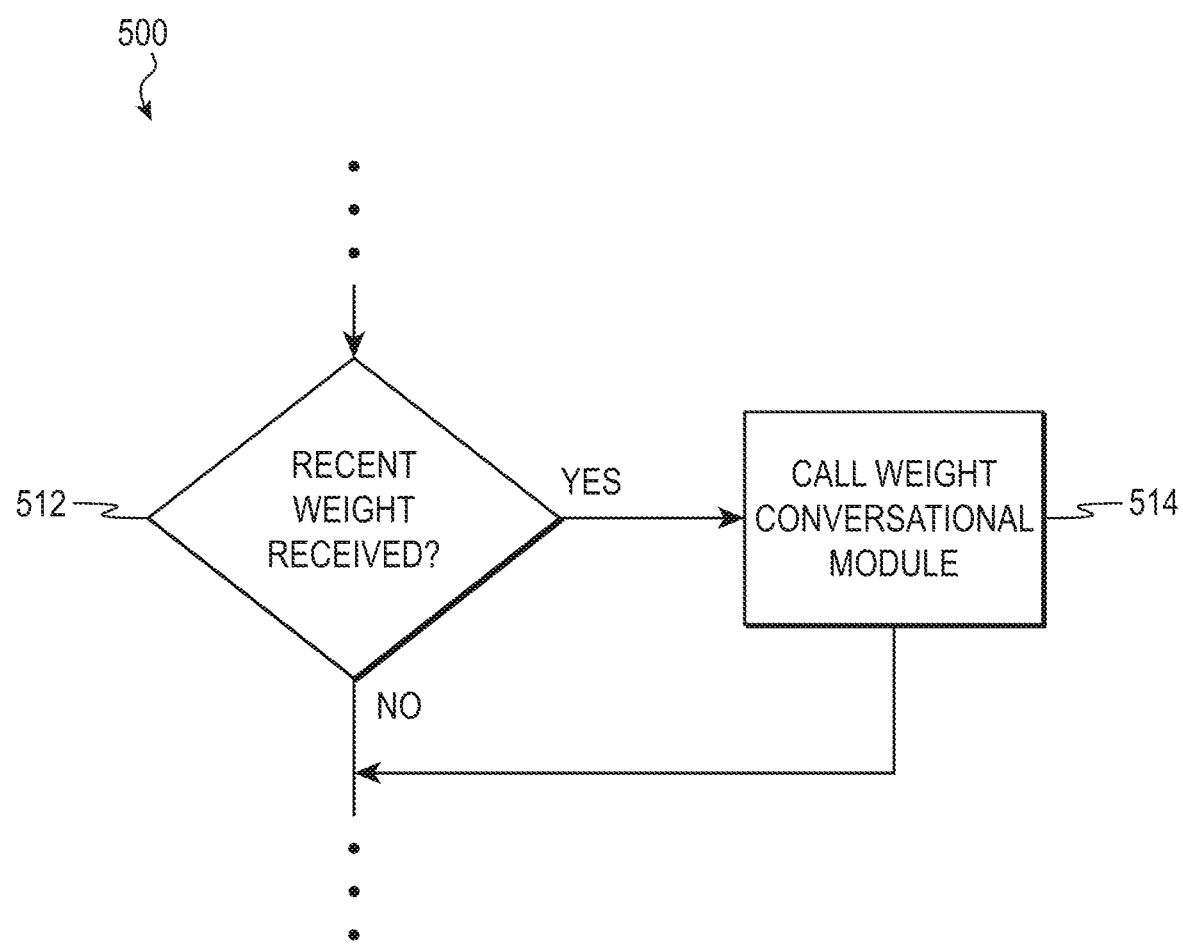
FIG. 5A depicts a second example decision block. This second example decision block may be used in a flow engine, such as the example flow engine of FIG. 3.

FIG. 5A depicts a second example decision block 500. This second example decision block 500 may be used in a flow engine, such as the example flow engine 300 of FIG. 3.

This second example decision block 500 includes a decision node 512. In this example, the decision node 512 may be gated according to whether or not a recent weight is received for the person, such as from a digital scale operable to communicate with one or more background process that execute the decision node 512 and/or an associated database, a wearable device configured to communicate with a digital scale, a medical provider's system that is configured to communicate with the background process, and so on. If so, the flow may proceed to an action node 514 where the background process may call a weight conversational module before the flow returns to a decision node, action node, and/or other point subsequent to the decision node 512. Otherwise the flow may directly proceed to a decision node, action node, and/or other point subsequent to the decision node 512.

Although the second example decision block 500 is illustrated and described as including a particular series of operations performed in a particular order, it is understood that this is an example. In any number of implementations, various orders of the same, similar, and/or different operations may be used without departing from the scope of the present disclosure.

For example, the decision node 512 is illustrated and described as gating according to whether or not a recent weight is received for the person. However, it is understood that this is an example. In other implementations, the decision node 512 may follow an action node that prompts the person for a recent weight and the decision node 512 may be gated according to whether or not the person provides a recent weight in response to the prompt. Various configurations are possible and contemplated without departing from the scope of the present disclosure.

By way of another example, the decision node 512 is illustrated and described as gating according to whether or not a recent weight is received for the person. However, it is understood that this is an example. In other implementations, the decision node 512 may be gated according to whether or not any clinically relevant data point is received from any kind of device. Various configurations are possible and contemplated without departing from the scope of the present disclosure.

Figure 5B:
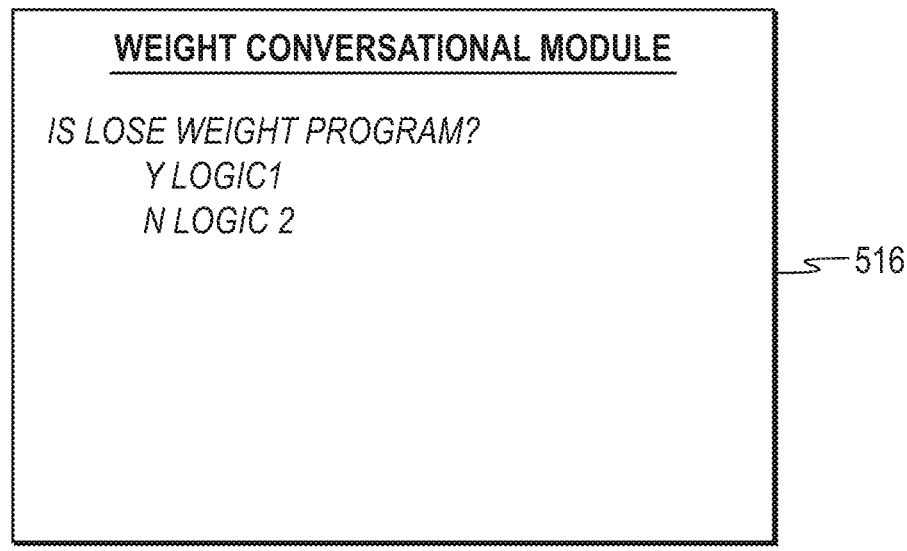
FIG. 5B depicts a first example conversational module. This first example conversational module may be used with the second example decision block of FIG. 5A and/or the system of FIG. 1

FIG. 5B depicts a first example conversational module 516. This first example conversational module 516 may be used with the second example decision block 500 of FIG. 5A and/or the system of FIG. 1. This first example conversational module 516 may be executed and/or otherwise used by one or more services.

As described above, conversational modules may enable people to engage in a back-and-forth conversation with one or more backend processes. This back-and-forth conversation may enable the people and/or the backend process to give and receive details and directives pertaining to associated programs, goals, missions, wellness habits, user actions, user needs, user interests, user questions, empathy, and so on. As further described above, some conversational modules may be dedicated to particular programs, goals, features, or missions whereas other conversational modules may be usable with multiple programs, goals, or missions, such as by including decision points that are gated to different instructions or computer code using logic, algorithms, heuristics, data, artificial intelligence, and/or machine learning according to the occurrence of various events, the program that is configured for a person, one or more of the goals that are configured for the person, whether one or more of the goals that are configured for the person are primary or secondary, whether one or more of the goals that are configured for the person are required or optional, whether one or more features are active (which may be activated according to the program that is configured for the person, one or more of the goals that are configured for the person, and so on), actions the person has taken, received data for the person, and so on.

This first example conversational module 516 may be gated according to whether or not a lose weight goal is configured for the person. If so, this first example conversational module 516 may gate to a first logic, computer code, and/or artificial intelligence and/or machine learning sequence. Otherwise, this first example conversational module 516 may gate to a second logic, computer code, and/or artificial intelligence and/or machine learning sequence.

Although this first example conversational module 516 is illustrated and described as including a particular series of operations performed in a particular order, it is understood that this is an example. In any number of implementations, various orders of the same, similar, and/or different operations may be used without departing from the scope of the present disclosure.

For example, this first example conversational module 516 is illustrated as either gating to a first logic or a second logic according to whether or not a lose weight goal is configured for the person. However, it is understood that this is an example. In other implementations, this first example conversational module 516 may instead gate according to artificial intelligence and/or machine learning. Various configurations are possible and contemplated without departing from the scope of the present disclosure.

Figure 6A:
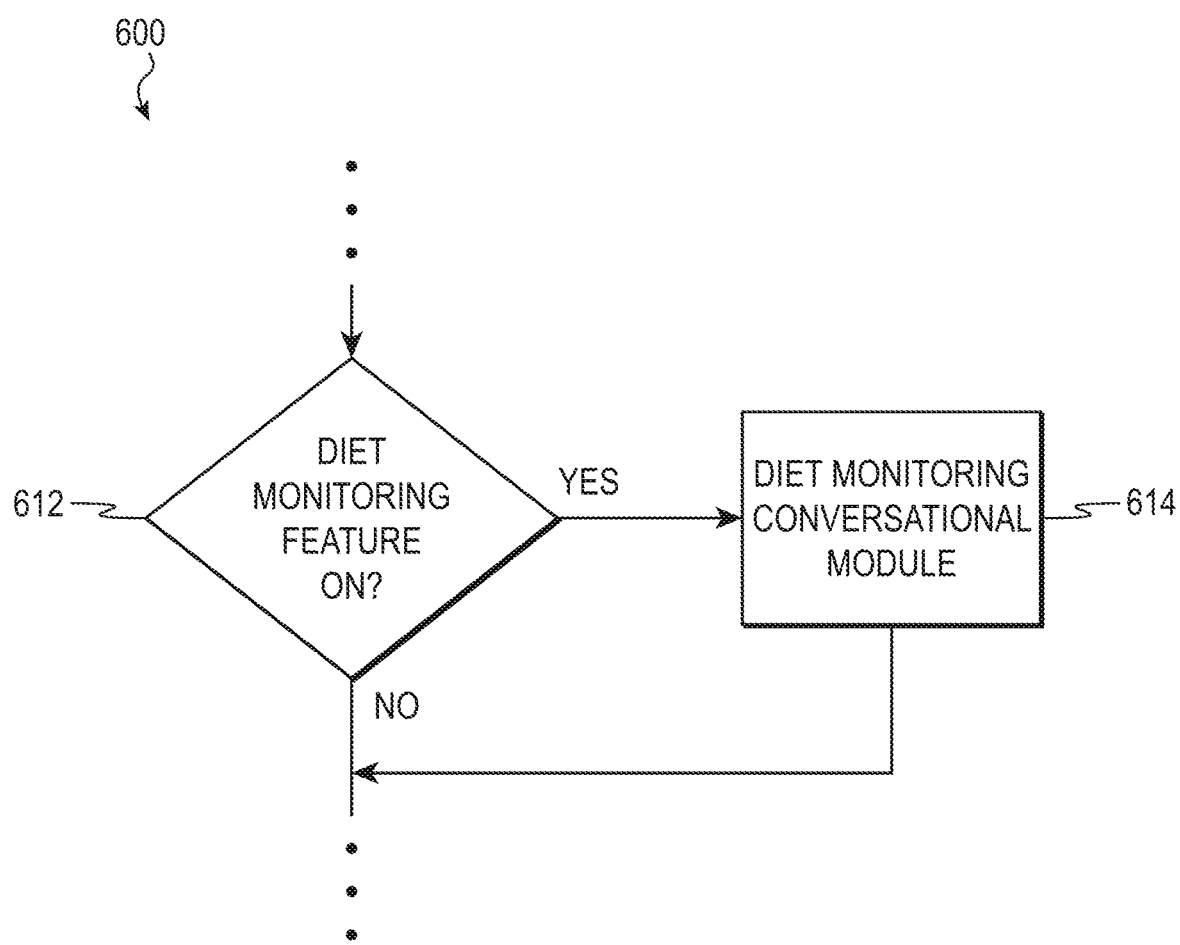
FIG. 6A depicts a third example decision block. This third example decision block may be used in a flow engine, such as the example flow engine of FIG. 3.

FIG. 6A depicts a third example decision block 600. This third example decision block 600 may be used in a flow engine, such as the example flow engine 300 of FIG. 3.

This third example decision block 600 includes a decision node 612. In this example, the decision node 612 may be gated according to whether or not a diet monitoring feature is on. In some examples, the diet monitoring feature may be turned on according to a program that is configured for the person, one or more goals that are configured for the person, one or more missions that are configured for the person, options selected by the person, options selected for the person, and so on. If so, the flow may proceed to an action node 614 where the background process may call a diet monitoring conversational module before the flow to a decision node, action node, and/or other point subsequent to the decision node 612. Otherwise the flow may directly proceed to a decision node, action node, and/or other point subsequent to the decision node 612.

Although the third example decision block 600 is illustrated and described as including a particular series of operations performed in a particular order, it is understood that this is an example. In any number of implementations, various orders of the same, similar, and/or different operations may be used without departing from the scope of the present disclosure.

For example, the decision node 612 is illustrated and described as gating according to whether or not a diet monitoring feature is on. However, it is understood that this is an example. In other implementations, the decision node 612 may instead determine whether or not to turn such a diet monitoring feature on, such as according to a program that is configured for the person, one or more goals that are configured for the person, one or more missions that are configured for the person, options selected by the person, options selected for the person, and so on. Various configurations are possible and contemplated without departing from the scope of the present disclosure.

Figure 6B:
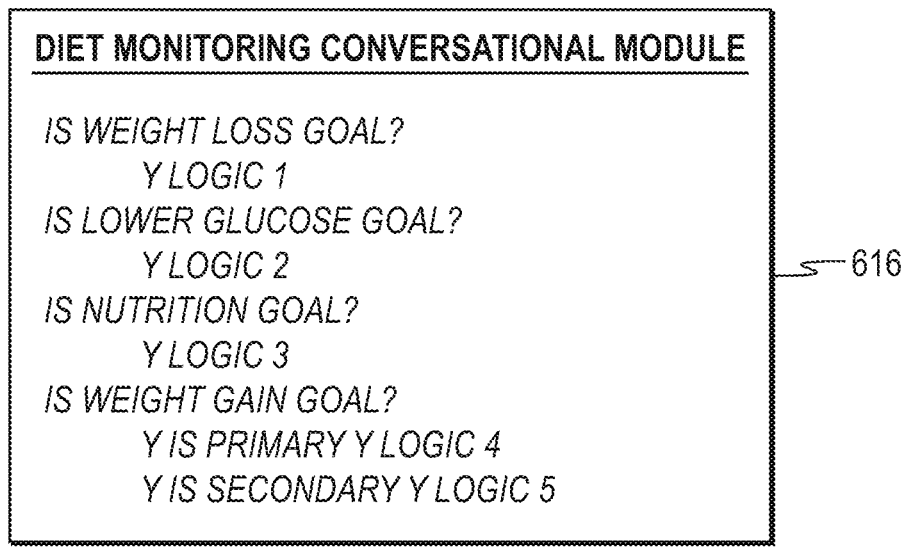
FIG. 6B depicts a second example conversational module. This second example conversational module may be used with the third example decision block of FIG. 6A and/or the system of FIG. 1.

FIG. 6B depicts a second example conversational module 616. This second example conversational module 616 may be used with the third example decision block 600 of FIG. 6A and/or the system 100 of FIG. 1. This second example conversational module 616 may be executed and/or otherwise used by one or more services.

This second example conversational module 616 may be gated according to whether specific goals are configured for the person. This first example conversational module 516 may gate to a first logic, computer code, and/or artificial intelligence and/or machine learning sequence if a set of features that collectively define a targeted treatment that helps serve an aim of weight loss is configured for the person, a second logic, computer code, and/or artificial intelligence and/or machine learning sequence if a set of features that collectively define a targeted treatment that helps serve an aim of lowing glucose is configured for the person, a third logic, computer code, and/or artificial intelligence and/or machine learning sequence if a set of features that collectively define a targeted treatment that helps serve an aim related to nutrition is configured for the person, a fourth logic, computer code, and/or artificial intelligence and/or machine learning sequence if a set of features that collectively define a targeted treatment that helps serve an aim of weight gain is configured as primary for the person, and a fifth logic, computer code, and/or artificial intelligence and/or machine learning sequence if the set of features that collectively define the targeted treatment that helps serve the aim of weight gain is configured as secondary for the person.

Although this second example conversational module 616 is illustrated and described as including a particular series of operations performed in a particular order, it is understood that this is an example. In any number of implementations, various orders of the same, similar, and/or different operations may be used without departing from the scope of the present disclosure.

For example, this second example conversational module 616 is illustrated and described as gating according to whether specific goals are configured for the person. However, it is understood that this is an example. In other implementations, this second example conversational module 616 may gate to a sixth logic, computer code, and/or artificial intelligence and/or machine learning sequence if none of the specified goals are configured for the person. Various configurations are possible and contemplated without departing from the scope of the present disclosure.

Figure 7A:
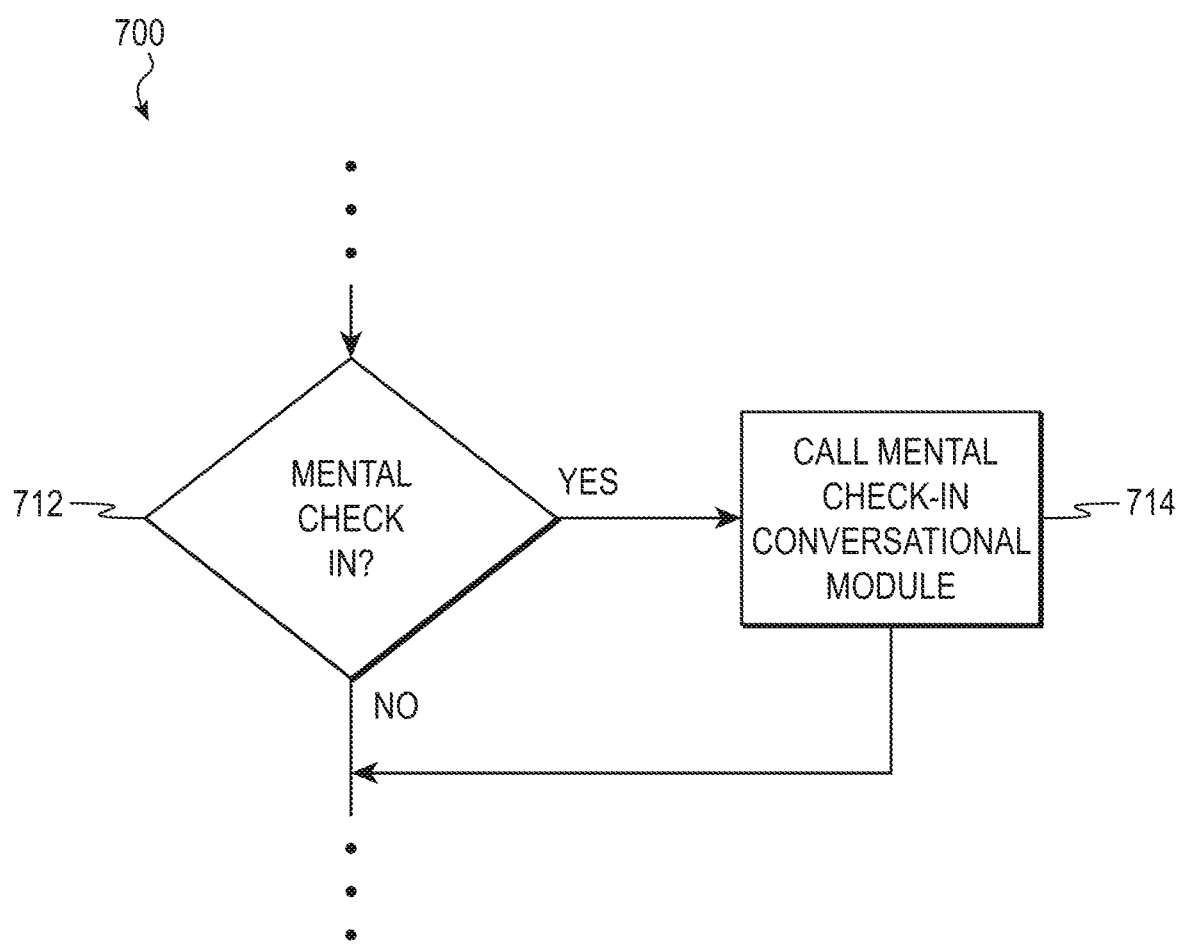
FIG. 7A depicts a fourth example decision block. This fourth example decision block may be used in a flow engine, such as the example flow engine of FIG. 3.

FIG. 7A depicts a fourth example decision block 700. This fourth example decision block 700 may be used in a flow engine, such as the example flow engine 300 of FIG. 3.

This fourth example decision block 700 includes a decision node 712. In this example, the decision node 712 may be gated according to whether or not to perform a mental check-in. In some examples, one or more background processes may determine whether or not to perform the mental check-in according to results of previous mental check-ins, mental warning flags, risk factors, a program that is configured for the person, one or more goals that are configured for the person, one or more missions that are configured for the person, options selected by the person, options selected for the person, and so on. If so, the flow may proceed to an action node 714 where the background process may call a mental check-in conversational module before the flow returns to a decision node, action node, and/or other point subsequent to the decision node 712. Otherwise the flow may directly proceed to a decision node, action node, and/or other point subsequent to the decision node 712.

Although the fourth example decision block 700 is illustrated and described as including a particular series of operations performed in a particular order, it is understood that this is an example. In any number of implementations, various orders of the same, similar, and/or different operations may be used without departing from the scope of the present disclosure.

For example, the action node 714 is illustrated and described as returning to a decision node, action node, and/or other point subsequent to the decision node 712. However, it is understood that this is an example. In other implementations, the decision node 712 may instead determine that the person's response and/or responses to the mental check-in conversational module merit immediately ending and summoning assistance for the person rather than calling any other conversational module. Various configurations are possible and contemplated without departing from the scope of the present disclosure.

Figure 7B:
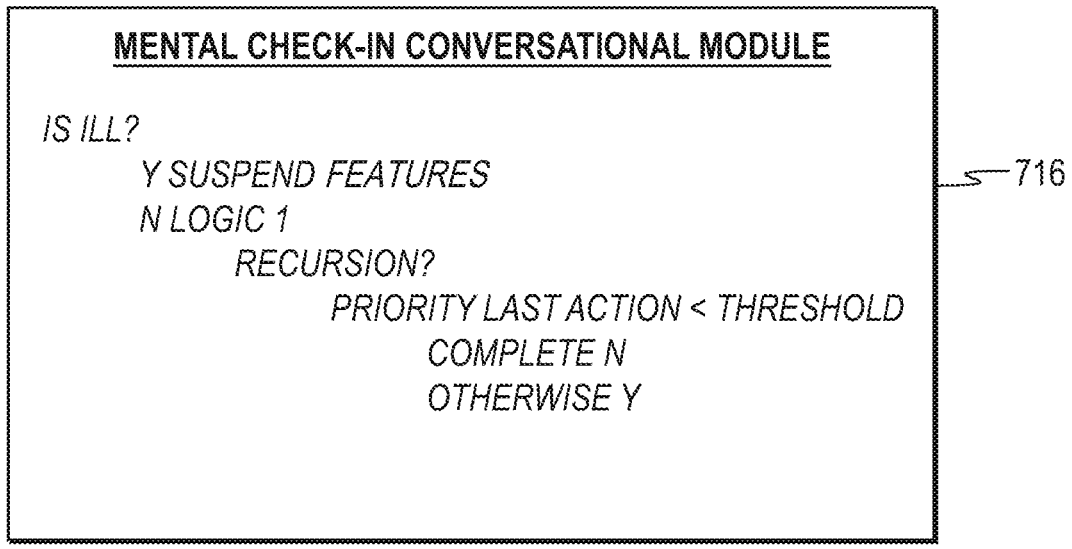
FIG. 7B depicts a third example conversational module. This third example conversational module may be used with the fourth example decision block of FIG. 7A and/or the system of FIG. 1

FIG. 7B depicts a third example conversational module 716. This third example conversational module 716 may be used with the fourth example decision block 700 of FIG. 7A and/or the system 100 of FIG. 1. This third example conversational module 716 may be executed and/or otherwise used by one or more services.

This third example conversational module 716 may be gated according to whether or not the person responds that they are ill. If so, this third example conversational module 716 may suspend one or more features (such as missions, weight check features, conversation modules, and so on) due to the illness. Otherwise, this third example conversational module 716 may gate to a first logic, computer code, and/or artificial intelligence and/or machine learning sequence.

This first logic, computer code, and/or artificial intelligence and/or machine learning sequence may enable the person to engage in a back-and-forth conversation with one or more backend processes related to the person's mental state. This first logic, computer code, and/or artificial intelligence and/or machine learning sequence may also include a section that may be repetitively reevaluated. For example, this first logic, computer code, and/or artificial intelligence and/or machine learning sequence may also recursively call the third example conversational module 716 so that the back-and-forth conversation may continue beyond the first logic, computer code, and/or artificial intelligence and/or machine learning sequence according to responses the person provided on one or more previous calls of this third example conversational module.

However, the first logic, computer code, and/or artificial intelligence and/or machine learning sequence may assign priorities to the interaction that the first logic, computer code, and/or artificial intelligence and/or machine learning sequence provides before recursively calling the third example conversational module 716 and may omit recursively calling the third example conversational module 716 when the priority of that last action meets or exceeds a threshold (and/or otherwise repetitively reevaluating, such as via a repeated block of code that may be exited when the priority exceeds the threshold). In this way, the first logic, computer code, and/or artificial intelligence and/or machine learning sequence may emphasize that last action by ending the third example conversational module 716 after that last action instead of continuing the back-and-forth conversation afterward but may continue recursively calling the third example conversational module 716 after performing other actions.

Although this third example conversational module 716 is illustrated and described as including a particular series of operations performed in a particular order, it is understood that this is an example. In any number of implementations, various orders of the same, similar, and/or different operations may be used without departing from the scope of the present disclosure.

For example, this third example conversational module 716 is illustrated and described as recursively calling the third example conversational module 716 (and/or otherwise performing a repetitive reevaluation) so that the back-and-forth conversation may continue beyond the first logic, computer code, and/or artificial intelligence and/or machine learning sequence according to responses the person provided on one or more previous calls of this third example conversational module. However, it is understood that this is an example. In other implementations, this third example conversational module 716 may instead end after executing the first logic, computer code, and/or artificial intelligence and/or machine learning sequence. Various configurations are possible and contemplated without departing from the scope of the present disclosure.

By way of another example, this third example conversational module 716 is illustrated and described as recursively calling the third example conversational module 716 (and/or otherwise performing a repetitive reevaluation) when the priority of the last action satisfies a threshold. However, it is understood that this is an example. In other implementations, this third example conversational module 716 may instead end after determining that a threshold number of iterations have been performed. By way of illustration, the threshold number of iterations may be set to prevent the person from being burdened or tiring of the third example conversational module 716. Various configurations are possible and contemplated without departing from the scope of the present disclosure.

Figure 8A:
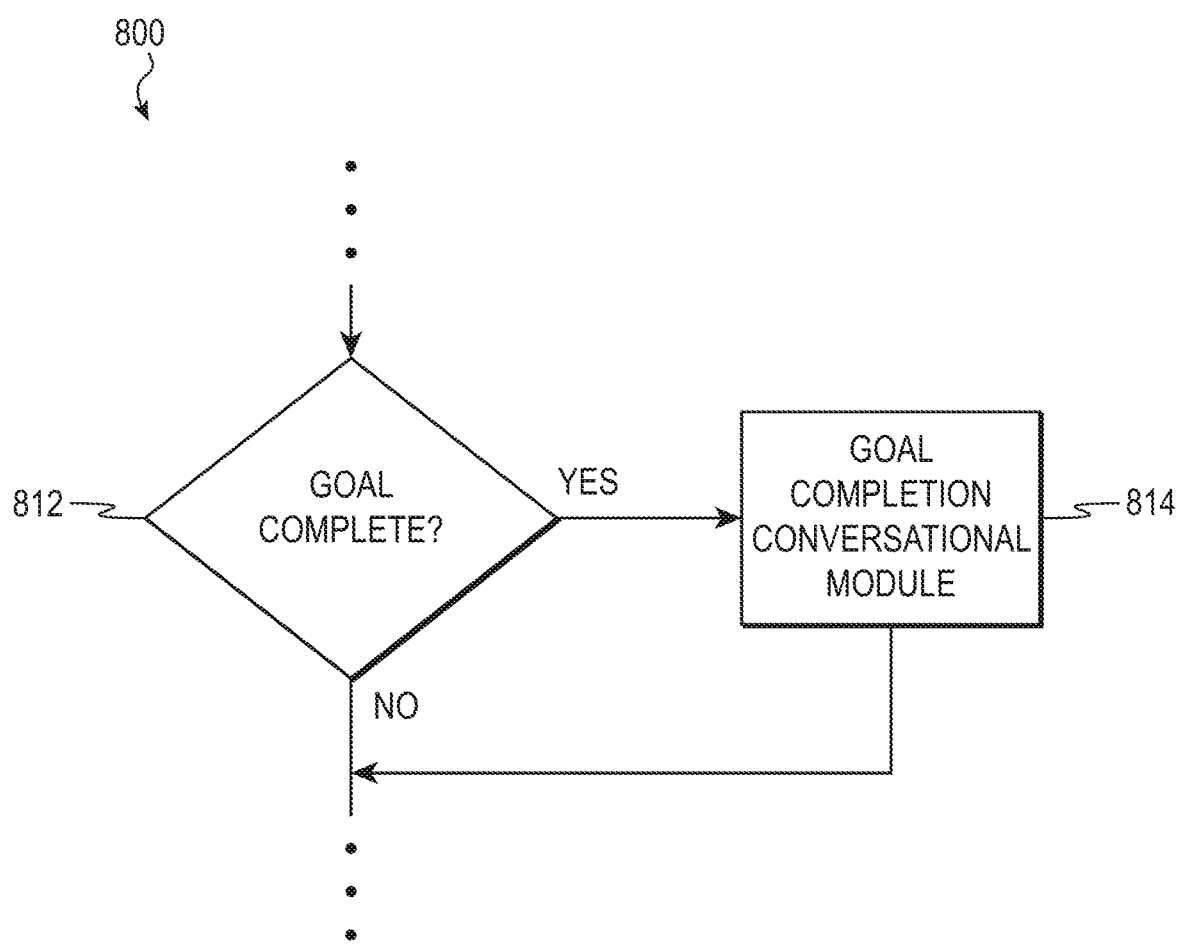
FIG. 8A depicts a fifth example decision block. This fifth example decision block may be used in a flow engine, such as the example flow engine of FIG. 3.

FIG. 8A depicts a fifth example decision block 800. This fifth example decision block 800 may be used in a flow engine, such as the example flow engine 300 of FIG. 3.

This fifth example decision block 800 includes a decision node 812. In this example, the decision node 812 may be gated according to whether or not a goal is complete for the person. If so, the flow may proceed to an action node 814 where the background process may call a goal completion conversational module before the flow returns to a decision node, action node, and/or other point subsequent to the decision node 812. Otherwise the flow may directly proceed to a decision node, action node, and/or other point subsequent to the decision node 812.

Although the fifth example decision block 800 is illustrated and described as including a particular series of operations performed in a particular order, it is understood that this is an example. In any number of implementations, various orders of the same, similar, and/or different operations may be used without departing from the scope of the present disclosure.

For example, the decision node 812 is illustrated and described as proceeding to the action node 814 where the background process calls a goal completion conversational module. However, it is understood that this is an example. In other implementations, the decision node 812 may instead gate to another decision node where the background process determines whether or not a specific goal is complete before proceeding to an action node that calls a specific goal completion conversational module for the specific completed goal. Various configurations are possible and contemplated without departing from the scope of the present disclosure.

Figure 8B:
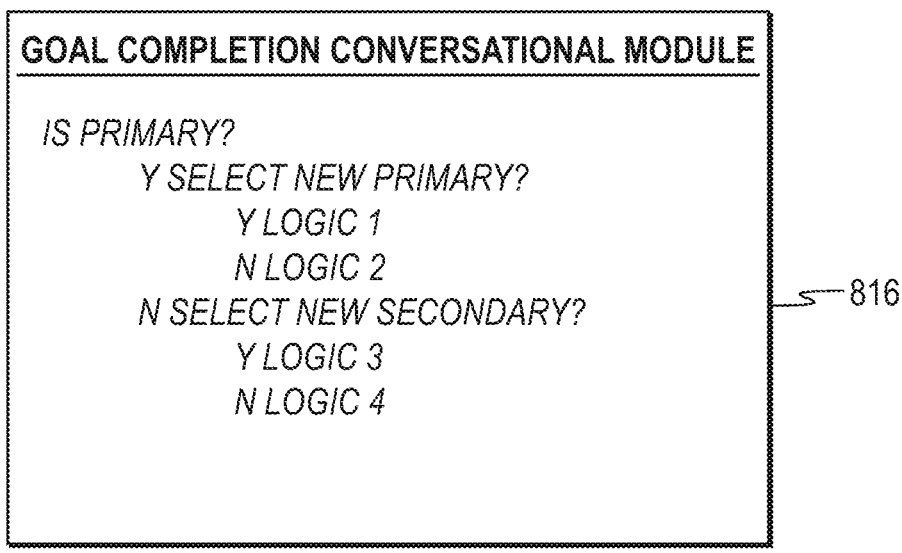
FIG. 8B depicts a fourth example conversational module. This fourth example conversational module may be used with the fifth example decision block of FIG. 8A and/or the system of FIG. 1.

FIG. 8B depicts a fourth example conversational module 816. This fourth example conversational module 816 may be used with the fifth example decision block 800 of FIG. 8A and/or the system 100 of FIG. 1. This fourth example conversational module 816 may be executed and/or otherwise used by one or more services.

This fourth example conversational module 816 may be gated according to whether or not a completed goal is primary for the person. If so, this fourth example conversational module 816 may gate to a first logic, computer code, and/or artificial intelligence and/or machine learning sequence if the background process and/or the person is to select a new primary goal and to a second logic, computer code, and/or artificial intelligence and/or machine learning sequence if one or more background processes and/or the person is not to select a new primary goal. For example, the fourth example conversational module 816 may determine the person will select a new primary goal if the person responds positively to a prompt that the person wishes to select a new primary goal. Otherwise, this fourth example conversational module 816 may gate to a third logic, computer code, and/or artificial intelligence and/or machine learning sequence if the background process and/or the person is to select a new secondary goal and to a fourth logic, computer code, and/or artificial intelligence and/or machine learning sequence if the background process and/or the person is not to select a new secondary goal. For example, the fourth example conversational module 816 may determine the person will select a new secondary goal if the person responds positively to a prompt that the person wishes to select a new secondary goal.

Although this fourth example conversational module 816 is illustrated and described as including a particular series of operations performed in a particular order, it is understood that this is an example. In any number of implementations, various orders of the same, similar, and/or different operations may be used without departing from the scope of the present disclosure.

For example, this fourth example conversational module 816 is illustrated as determining whether or not to select new primary or secondary goals. However, it is understood that this is an example. In other implementations, this fourth example conversational module 816 may instead assign new primary or secondary goals to the person. Various configurations are possible and contemplated without departing from the scope of the present disclosure.

Figure 9:
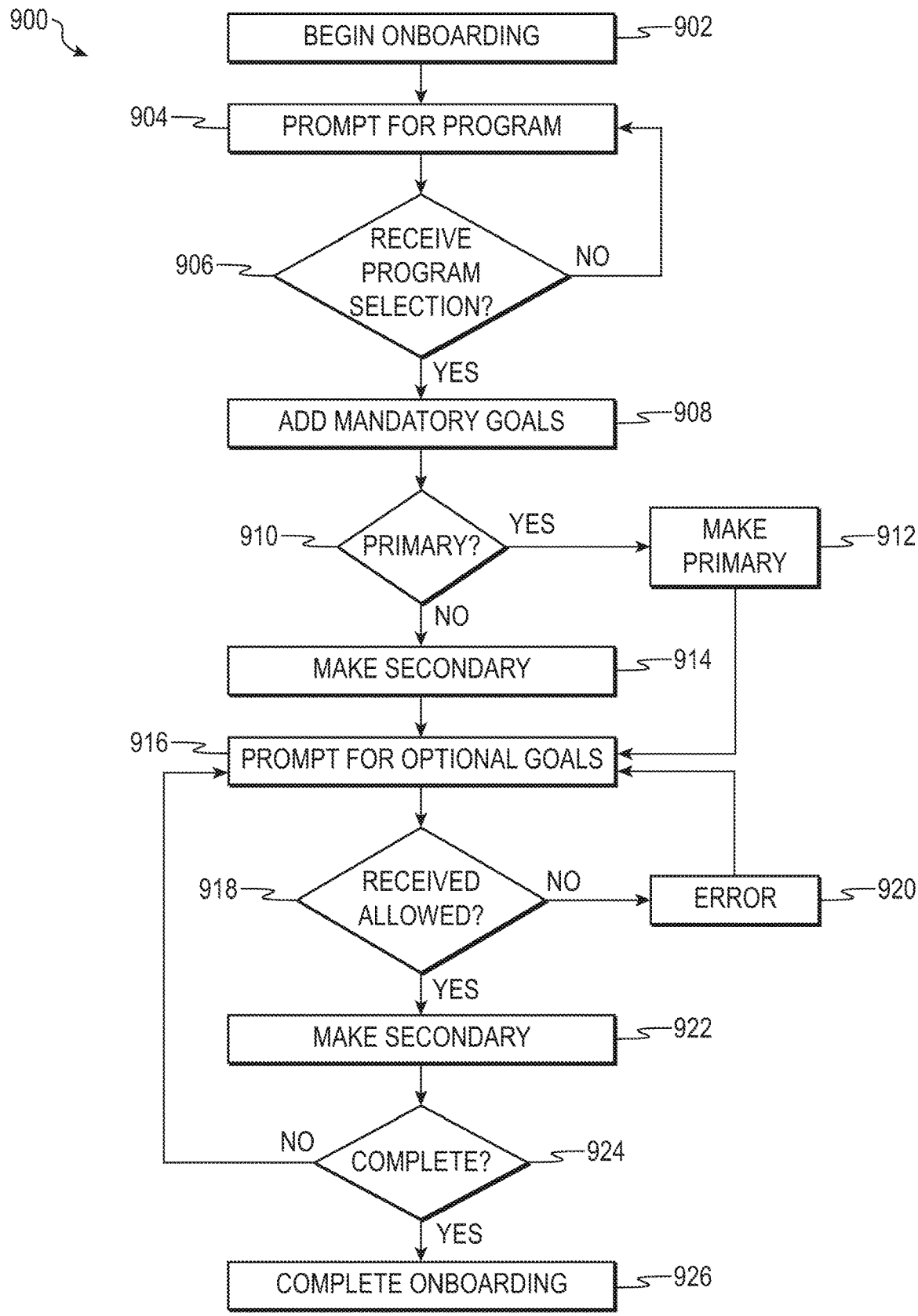
FIG. 9 is a flow chart illustrating a first example method for onboarding a person in a system for providing artificial intelligence health support. The method may be performed by the system of FIG. 1.

FIG. 9 is a flow chart illustrating an example method 900 for onboarding a person in a system for providing artificial intelligence health support. The method 900 may be performed by the system 100 of FIG. 1.

At operation 902, an electronic device (such as the server 104 of FIG. 1) may begin onboarding a person in a system for providing artificial intelligence health support. The flow may then proceed to operation 904 where the electronic device may prompt for a program. Next, the flow may proceed to operation 906 where the electronic device may determine whether or not a program selection is received. If not, the flow may return to operation 904 where the electronic device may again prompt for a program. Otherwise, the flow may proceed to operation 908.

At operation 908, the electronic device may add one or more mandatory goals that are associated with the selected program. The flow may then proceed to operation 910 where the electronic device determines whether the goal is to be made primary or secondary. If the goal is to be made primary, the flow may proceed to operation 912 where the goal is made primary before the flow proceeds to operation 916. Otherwise, the flow may proceed to operation 914 where the goal is made secondary before the flow proceeds to operation 916.

At operation 916, the electronic device may prompt for one or more optional goals. The flow may then proceed to operation 918 where the electronic device may determine whether or not received optional goals are allowed. If not, the flow may proceed to operation 920 where the electronic device may determine that an error has occurred before returning to operation 916 and again prompting for one or more optional goals. Otherwise, the flow may proceed to operation 922 where the electronic device makes the one or more selected optional goals secondary before the flow proceeds to operation 924.

At operation 924, the electronic device determines whether or not the onboarding process is complete. If not, the flow may proceed to operation 916 where the electronic device again prompts for one or more optional goals. Otherwise, the flow may proceed to operation 926 where the electronic device may complete the onboarding process. This may involve storing data regarding any mandatory goals, optional goals, primary goals, secondary goals, and/or any other data related to the onboarding in user information that is stored in user progress in one or more databases, which may be accessed while providing artificial intelligence health support for the person.

In various examples, this example method 900 may be implemented using a group of interrelated software modules or components that perform various functions discussed herein. These software modules or components may be executed within a cloud network and/or by one or more computing devices, such as the server 104 of FIG. 1.

Although the example method 900 is illustrated and described as including particular operations performed in a particular order, it is understood that this is an example. In various implementations, various orders of the same, similar, and/or different operations may be performed without departing from the scope of the present disclosure.

For example, the method 900 is illustrated and described at operations 910, 912, and 914 as determining whether or not to make a single goal primary or secondary. However, it is understood that this is an example. In other implementations, the method 900 may determine which among multiple goals is to be made primary or secondary. Various configurations are possible and contemplated without departing from the scope of the present disclosure.

Further, the method 900 is illustrated and described at operations 910, 912, and 914 as determining whether or not to make one of the mandatory goals primary or secondary. However, it is understood that this is an example. In other implementations, the method 900 may make an optional goal primary. Various configurations are possible and contemplated without departing from the scope of the present disclosure.

Additionally, the method 900 is illustrated and described at 916, 918, and 920 as determining whether or not received optional goals are allowed. However, it is understood that this is an example. In various implementations, optional goals that are not allowed may not be selectable at all so the method 900 may omit determining whether or not received optional goals are allowed. Various configurations are possible and contemplated without departing from the scope of the present disclosure.

Moreover, the method 900 is illustrated and described as onboarding a single person. However, it is understood that this is an example. In various implementations, a group of people may be onboarded. By way of illustration, a group of people insured by an insurer, patients of a doctor or hospital, employees of a company or other business, and so on may all be onboarded. Various configurations are possible and contemplated without departing from the scope of the present disclosure.

In various implementations, a system for interacting with a database to provide artificial intelligence health support for people may include a memory allocation configured to store at least one executable asset and a processor allocation configured to access the memory allocation and execute the at least one executable asset to instantiate a conversational service and an artificial intelligence health support service. The conversational service may render a first specific, targeted treatment for a first person in association with a first program that is configured for the first person using a conversational module of conversational modules and first user information retrieved from the database and render a second specific, targeted treatment for a second person in association with a second program that is configured for the second person using the conversational module of the conversational modules includes first instructions to perform for the first program and second instructions to perform for the second program. The artificial intelligence health support service may track the first specific, targeted treatment in first user progress stored in the database and track the first specific, targeted treatment in second user progress stored in the database.

In some examples, the conversational module may be a first conversational module and the conversational service may further render the first specific, targeted treatment for the first person using a second conversational module that is dedicated to the first program. In various such examples, the conversational service may further render the second specific, targeted treatment for the second person using a third conversational module that is dedicated to the second program.

In a number of examples, the conversational module may be a first conversational module and the conversational service may further render the first specific, targeted treatment for the first person using a second conversational module when a feature is active. In various examples, at least one of the conversational modules may perform a set of instructions repetitiously. In some examples the conversational module may be a first conversational module and the conversational service may further render the first specific, targeted treatment for the first person using a second conversational module upon receiving data regarding activity for the first person. In a number of examples, at least one of the conversational modules may be operable to change the first program for the first person.

In some embodiments, a system for interacting with a database to provide artificial intelligence health support for people may include a memory allocation configured to store at least one executable asset and a processor allocation configured to access the memory allocation and execute the at least one executable asset to instantiate a conversational service and an artificial intelligence health support service. The conversational service may render a specific, targeted treatment for a first person and a second person using a conversational module of conversational modules and first user information for the first person and second user information for the second person retrieved from the database. The conversational module may include first instructions to perform for a first goal configured for the first person and second instructions to perform for a second goal configured for the second person. The artificial intelligence health support service may track the specific, targeted treatment in first user progress and second user progress stored in the database.

In various examples, at least one of the conversational modules may be operable to change the first goal for the first person. In some examples, the conversational module may be a first conversational module and the conversational service may further render the specific, targeted treatment for the first person or the second person using a second conversational module upon receiving data regarding activity for the first person or the second person. In a number of examples, at least one of the conversational modules may perform a set of instructions repetitiously when a priority of a previous action is below a threshold.

In some examples, the conversational module may be a first conversational module and the conversational service may further render the specific, targeted treatment for the first person or the second person using a second conversational module when a feature is active. In a number of examples, the conversational module may be a first conversational module and the conversational service may further render the specific, targeted treatment for the first person using a second conversational module that is dedicated to the first goal. In various such examples, the conversational service may further render the specific, targeted treatment for the second person using a third conversational module that is dedicated to the second goal.

In a number of embodiments, a system for interacting with a database to provide artificial intelligence health support for people may include a memory allocation configured to store at least one executable asset and a processor allocation configured to access the memory allocation and execute the at least one executable asset to instantiate a conversational service and an artificial intelligence health support service. The conversational service may render a specific, targeted treatment for a first person and a second person using first user information for the first person and second user information for the second person retrieved from the database by using a flow engine and at least one of the conversational modules. The flow engine may include first instructions to perform for a first program or a first goal configured for the first person and second instructions to perform for a second program or a second goal configured for the second person. The artificial intelligence health support service may track the specific, targeted treatment in first user progress and second user progress stored in the database.

In various examples, the first program or the first goal configured for the first person may be the first program, the second program of the second goal configured for the second person may be the second program, the flow engine may further include third instructions to perform for the first goal configured for the first person, and the flow engine may further include fourth instructions to perform for the second goal configured for the second person. In some examples, the flow engine may include a third set of instructions to perform for the first person and the second person regardless of any program or goal configured for the first person or the second person.

In a number of examples, the flow engine may include third instructions to perform when a feature is active. In various such examples, the feature may be activated upon configuration of the first goal or the first program for the first person. In some examples, the flow engine may include third instructions to perform upon receiving data regarding activity for the first person or the second person.

In various implementations, a system for interacting with a database to provide artificial intelligence health support for people may include a memory allocation configured to store at least one executable asset and a processor allocation configured to access the memory allocation and execute the at least one executable asset to instantiate an onboarding service and an artificial intelligence health support service. The onboarding service may configure user information stored in the database for a person using a program of multiple programs, at least one of multiple goals, and at least one of multiple missions. The artificial intelligence health support service may retrieve the user information for the person from the database; render specific, targeted treatment for the person in association with the program that is configured for the person; and track the specific, targeted treatment in user progress stored in the database.

In some examples, the onboarding service may configure the user information for the person using a first goal of the multiple goals and a second goal of the multiple goals. In various such examples, the onboarding service may configure the first goal as primary and the second goal as secondary. In some such examples, the onboarding service may select the at least one of the multiple missions according to an association between the first goal and the at least one of the multiple missions because the first goal is primary. In a number of such examples, the artificial intelligence health support service may configure another goal as primary after completion of the first goal. In various such examples, the first goal may be mandatory for the program. In a number of such examples, the second goal may be optional for the program.

In some implementations, a system for interacting with a database to provide artificial intelligence health support for people may include a memory allocation configured to store at least one executable asset and a processor allocation configured to access the memory allocation and execute the at least one executable asset to instantiate an onboarding service and an artificial intelligence health support service. The onboarding service may configure first user information stored in the database for a first person using a first program of multiple programs, at least a first goal of multiple goals, and at least a first mission of multiple missions and configure second user information stored in the database for a second person using a second program of the multiple programs, at least the first goal of the multiple goals, and at least one of the multiple missions. The artificial intelligence health support service may retrieve the first user information for the first person from the database; render specific, targeted first treatment for the first person in association with the first program that is configured for the first person; track the specific, targeted first treatment in first user progress stored in the database; retrieve the second user information for the second person from the database; render specific, targeted second treatment for the second person in association with the second program that is configured for the second person; and track the specific, targeted second treatment in second user progress stored in the database.

In various examples, a mission of the multiple missions may be associated with at least the first goal and a second goal of the multiple goals. In some examples, the onboarding service may prevent the first program from being used with a second goal of the multiple goals. In a number of examples, the onboarding service may prevent the first program from being used with a mission of the multiple missions.

In some examples, the artificial intelligence health support service may render the specific, targeted first treatment and the specific, targeted second treatment by calling a conversational service that is associated with the first goal. In a number of examples, the onboarding service may adjust a threshold associated with the first person based on a comorbidity associated with the first person. In some such examples, the threshold may be a nutritional threshold.

In a number of implementations, a system for interacting with a database to provide artificial intelligence health support for people may include a memory allocation configured to store at least one executable asset and a processor allocation configured to access the memory allocation and execute the at least one executable asset to instantiate an onboarding service and an artificial intelligence health support service. The onboarding service may configure first user information stored in the database for a first person using a program of multiple programs, at least a first goal of the multiple goals, and at least a first mission of the multiple missions and configure second user information stored in the database for a second person using the program of the multiple programs, at least a second goal of the multiple goals, and at least one of the multiple missions. The artificial intelligence health support service may retrieve the first user information for the first person from the database; render specific, targeted first treatment for the first person in association with the program that is configured for the first person; track the specific, targeted first treatment in first user progress stored in the database; retrieve the second user information for the second person from the database; render specific, targeted second treatment for the second person in association with the program that is configured for the second person; and track the specific, targeted second treatment in second user progress stored in the database.

In various examples, the at least one of the multiple missions may be the first mission. In some examples, the onboarding service may configure the first user information for the first person using the second goal as an optional goal. In a number of examples, the onboarding service may omit configuring the second user information for the second person using the second goal.

In some examples, the onboarding service may configure the first user information using the first goal for the first person based on a specification for the program and configure the second user information using the first goal and the second goal for the second person. In various examples, the onboarding service may configure the second user information using the second goal for the second person in response to input from the second person.

Although the above illustrates and describes a number of embodiments, it is understood that these are examples. In various implementations, various techniques and/or features of individual embodiments may be combined without departing from the scope of the present disclosure.

As described above and illustrated in the accompanying figures, the present disclosure relates to systems, methods, apparatuses, and computer program products for providing artificial intelligence health support for people. Specific, targeted treatments for people may be rendered by using a flow engine to call one or more conversational services. The specific, targeted treatments for the people may be tracked. The flow engine and/or one or more of the conversational services may include different instructions to perform for different programs and/or goals that have been configured for people. The flow engine and/or one or more of the conversational services may also include instructions to perform when certain features are active (which may be activated when certain programs and/or goals are configured for people), when data regarding activity for people are received, and so on. Other conversational services may be dedicated to particular programs and/or goals. Some conversational services may determine whether or not to perform various instructions repetitiously, such as determining not to perform such instructions repetitiously when a priority of a previous instruction is below a threshold.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A system, comprising:
a memory allocation configured to store at least one executable asset; and
a processor allocation configured to access the memory allocation and execute the at least one executable asset to instantiate at least one service that:
configures user information stored in a database for a person using a program of multiple programs, at least one of multiple goals, and at least one of multiple missions;
retrieves the user information for the person from the database;
renders specific, targeted treatment for the person in association with the program that is configured for the person using at least computer code that the at least one service also uses to render an additional specific, targeted treatment for an additional person in association with at least one of a different program, goal, or mission; and
tracks the specific, targeted treatment in user progress stored in the database.

2. The system of claim 1, wherein the at least one service configures the user information for the person using:
a first goal of the multiple goals; and
a second goal of the multiple goals.

3. The system of claim 2, wherein the first goal is mandatory for the program.

4. The system of claim 2, wherein the second goal is optional for the program.

5. The system of claim 2, wherein the at least one service configures the first goal as primary and the second goal as secondary.

6. The system of claim 5, wherein the at least one service selects the at least one of the multiple missions according to an association between the first goal and the at least one of the multiple missions because the first goal is primary.

7. The system of claim 5, wherein the at least one service configures another goal as primary after completion of the first goal.

8. A system, comprising:
a memory allocation configured to store at least one executable asset; and
a processor allocation configured to access the memory allocation and execute the at least one executable asset to:
configure first user information stored in a database for a first person using a first program of multiple programs, at least a first goal of multiple goals, and at least a first mission of multiple missions;
configure second user information stored in the database for a second person using a second program of the multiple programs, at least the first goal of the multiple goals, and at least one of the multiple missions;
retrieve the first user information for the first person from the database;
render specific, targeted first treatment for the first person in association with the first program that is configured for the first person;
track the specific, targeted first treatment in first user progress stored in the database;
retrieve the second user information for the second person from the database;
render specific, targeted second treatment for the second person in association with the second program that is configured for the second person using at least computer code that the at least one executable asset also uses to render the specific, targeted first treatment for the first person; and
track the specific, targeted second treatment in second user progress stored in the database.

9. The system of claim 8, wherein the processor allocation is further configured to access the memory allocation and execute the at least one executable asset to adjust a threshold associated with the first person based on a comorbidity associated with the first person.

10. The system of claim 9, wherein the threshold is a nutritional threshold.

11. The system of claim 8, wherein the processor allocation is further configured to access the memory allocation and execute the at least one executable asset to prevent the first program from being used with a second goal of the multiple goals.

12. The system of claim 8, wherein the processor allocation is further configured to access the memory allocation and execute the at least one executable asset to render the specific, targeted first treatment and the specific, targeted second treatment by calling a conversational service that is associated with the first goal.

13. The system of claim 8, wherein the processor allocation is further configured to access the memory allocation and execute the at least one executable asset to prevent the first program from being used with a mission of the multiple missions.

14. The system of claim 8, wherein a mission of the multiple missions is associated with at least the first goal and a second goal of the multiple goals.

15. A system, comprising:
a memory allocation configured to store at least one executable asset; and
a processor allocation configured to access the memory allocation and execute the at least one executable asset to:
configure first user information stored in a database for a first person using a program of multiple programs, at least a first goal of multiple goals, and at least a first mission of multiple missions;
configure second user information stored in the database for a second person using the program of the multiple programs, at least a second goal of the multiple goals, and at least one of the multiple missions;
retrieve the first user information for the first person from the database;

render specific, targeted first treatment for the first person in association with the program that is configured for the first person;

track the specific, targeted first treatment in first user progress stored in the database;

retrieve the second user information for the second person from the database;

render specific, targeted second treatment for the second person in association with the program that is configured for the second person using at least computer code that the at least one executable asset also uses to render the specific targeted first treatment for the first person; and track the specific, targeted second treatment in second user progress stored in the database.

16. The system of claim 15, wherein the processor allocation is further configured to access the memory allocation and execute the at least one executable asset to omit the configuring the second user information for the second person using the second goal.

17. The system of claim 15, wherein the at least one of the multiple missions is the first mission.

18. The system of claim 15, wherein the processor allocation is further configured to access the memory allocation and execute the at least one executable asset to configure the first user information for the first person using the second goal as an optional goal.

19. The system of claim 15, wherein the processor allocation is further configured to access the memory allocation and execute the at least one executable asset to configure the second user information using the second goal for the second person in response to input from the second person.

20. The system of claim 15, wherein the processor allocation is further configured to access the memory allocation and execute the at least one executable asset to:

configure the first user information using the first goal for the first person based on a specification for the program; and configure the second user information using the first goal and the second goal for the second person.

* * * * *